(12) United States Patent
Ammerman et al.

(10) Patent No.: US 10,758,286 B2
(45) Date of Patent: Sep. 1, 2020

(54) MINIMAL IMPACT ACCESS SYSTEM TO DISC SPACE

(71) Applicant: Benvenue Medical, Inc., Santa Clara, CA (US)

(72) Inventors: Joshua M. Ammerman, Bethesda, MD (US); Laurent B. Schaller, Los Altos, CA (US); Douglas M. Lorang, San Jose, CA (US); Ricardo J. Simmons, San Diego, CA (US); Timothy J. McGrath, Fond du Lac, WI (US)

(73) Assignee: Benvenue Medical, Inc., Santa Clara, CA (US)

( * ) Notice: Subject to any disclaimer, the term of this patent is extended or adjusted under 35 U.S.C. 154(b) by 121 days.

(21) Appl. No.: 15/927,460

(22) Filed: Mar. 21, 2018

(65) Prior Publication Data

US 2018/0271574 A1    Sep. 27, 2018

Related U.S. Application Data

(60) Provisional application No. 62/474,934, filed on Mar. 22, 2017.

(51) Int. Cl.
| | |
|---|---|
| *A61B 17/88* | (2006.01) |
| *A61B 17/70* | (2006.01) |
| *A61B 17/00* | (2006.01) |
| *A61B 17/02* | (2006.01) |
| *A61F 2/46* | (2006.01) |

(Continued)

(52) U.S. Cl.
CPC ........ *A61B 17/88* (2013.01); *A61B 17/00234* (2013.01); *A61B 17/025* (2013.01);
(Continued)

(58) Field of Classification Search
CPC . A61B 17/88; A61B 17/00234; A61B 17/025; A61B 17/7064; A61B 17/7071;
(Continued)

(56) References Cited

U.S. PATENT DOCUMENTS

| | | | | |
|---|---|---|---|---|
| 4,862,891 A | * | 9/1989 | Smith | ............... A61B 17/3417 |
| | | | | 606/191 |
| 5,201,742 A | * | 4/1993 | Hasson | ............. A61B 17/3403 |
| | | | | 606/1 |

(Continued)

*Primary Examiner* — Pedro Philogene
*Assistant Examiner* — David C Comstock
(74) *Attorney, Agent, or Firm* — Cook Alex Ltd.

(57) ABSTRACT

Methods and apparatus for accessing and repairing a vertebral disc include a pad with a central cut-out mounted to the skin of a patient or, alternatively, a pedicle-mounted support. An incision is made and then a corridor is created using an elongated guide and a series of dilating tubes. An access to the disc space is created through the superior articular process and the facet joint using the corridor defined by the dilating tubes. Nucleus material is removed from the disc space and the vertebral endplates are prepared. The disc space may be sized to select a suitable implant, which is advanced through the corridor and into the disc space following discectomy and endplate preparation. Bone graft material may be inserted into the disc space following installation of the implant and then posterior rigid fixation may be achieved using percutaneous pedicle screws, followed by closure of the site.

19 Claims, 20 Drawing Sheets

(51) Int. Cl.
*A61B 17/34* (2006.01)
*A61B 17/17* (2006.01)
*A61B 17/16* (2006.01)
*A61B 17/90* (2006.01)
*A61B 17/32* (2006.01)
*A61B 90/50* (2016.01)

(52) U.S. Cl.
CPC ...... *A61B 17/1671* (2013.01); *A61B 17/1757* (2013.01); *A61B 17/3417* (2013.01); *A61B 17/3421* (2013.01); *A61B 17/7064* (2013.01); *A61B 17/7071* (2013.01); *A61F 2/4601* (2013.01); *A61B 17/0293* (2013.01); *A61B 17/320016* (2013.01); *A61B 90/50* (2016.02); *A61B 2017/00261* (2013.01); *A61B 2017/00951* (2013.01); *A61B 2017/00991* (2013.01); *A61B 2017/0256* (2013.01); *A61B 2017/32006* (2013.01); *A61B 2017/3407* (2013.01); *A61B 2017/90* (2013.01)

(58) Field of Classification Search
CPC .. A61B 2017/00261; A61B 2017/0256; A61B 2017/90; A61B 2046/205; A61B 17/3403; A61B 17/3405; A61B 17/3407; A61F 2/4601
USPC .......... 600/204, 207, 231; 606/279; 604/104
See application file for complete search history.

(56) References Cited

U.S. PATENT DOCUMENTS

| | | |
|---|---|---|
| 5,549,679 A | 8/1996 | Kuslich |
| 5,571,189 A | 11/1996 | Kuslich |
| 6,228,022 B1* | 5/2001 | Friesem ............. A61B 17/1757 600/153 |
| 6,558,383 B2 | 5/2003 | Cunningham et al. |
| 7,087,058 B2 | 8/2006 | Cragg |
| 8,454,617 B2 | 6/2013 | Schaller et al. |
| 9,308,022 B2* | 4/2016 | Chitre ............... A61B 17/3417 |
| 9,480,574 B2 | 11/2016 | Lee et al. |
| 9,566,170 B2 | 2/2017 | Schell et al. |
| 10,258,228 B2* | 4/2019 | Genovese .......... A61B 17/7082 |
| 2005/0256525 A1* | 11/2005 | Culbert ................ A61K 31/713 606/53 |
| 2008/0015639 A1* | 1/2008 | Bjork ..................... A61B 17/17 606/240 |
| 2008/0294171 A1* | 11/2008 | Boehm, Jr. ............. A61F 2/446 606/90 |
| 2010/0228091 A1* | 9/2010 | Widenhouse ...... A61B 17/3423 600/203 |
| 2011/0144440 A1* | 6/2011 | Cropper ............. A61B 17/3421 600/203 |
| 2013/0282143 A1* | 10/2013 | Perkins ..................... A61F 2/80 623/36 |
| 2014/0163326 A1* | 6/2014 | Forsell ............... A61B 17/3423 600/207 |
| 2014/0235949 A1* | 8/2014 | Smith ................ A61B 17/3462 600/201 |
| 2016/0007979 A1* | 1/2016 | Bhagat ............... A61B 17/3403 604/175 |
| 2016/0008141 A1 | 1/2016 | Huffmaster et al. |
| 2016/0228261 A1 | 8/2016 | Emery et al. |
| 2016/0256148 A1 | 9/2016 | Huffmaster et al. |
| 2016/0367332 A1* | 12/2016 | Shah ....................... A61B 90/11 |
| 2017/0135704 A1* | 5/2017 | Abbasi ............... A61B 17/7035 |

* cited by examiner

MINIMAL IMPACT ACCESS SYSTEM TO DISC SPACE

CROSS REFERENCE TO RELATED APPLICATIONS

This application claims the benefit of and priority to U.S. Provisional Patent Application Ser. No. 62/474,934, filed Mar. 22, 2017, the contents of which are incorporated by reference herein.

BACKGROUND

Field of the Disclosure

The present invention generally relates to apparatus and methods employed in minimally invasive surgical ("MIS") procedures and more particularly to various aspects of apparatus and methods for separating and/or supporting tissue layers, especially in the disc space of the spine.

Description of Related Art

A variety of physical conditions involve two tissue surfaces that, for diagnosis or treatment of the condition, need to be separated or distracted or maintained in a separated condition from one another and then supported in a spaced-apart relationship. Such separation or distraction may be to gain exposure to selected tissue structures, to apply a therapeutic pressure to selected tissues, to return or reposition tissue structures to a more normal or original anatomic position and form, to deliver a drug or growth factor, to alter, influence or deter further growth of select tissues or to carry out other diagnostic or therapeutic procedures. Depending on the condition being treated, the tissue surfaces may be opposed or contiguous and may be bone, skin, soft tissue, or a combination thereof.

One location of the body where tissue separation is useful as a corrective treatment is in the spinal column. Developmental irregularities, trauma, tumors, stress and degenerative wear can cause defects in the spinal column for which surgical intervention is necessary. Some of the more common defects of the spinal column include vertebral compression fractures, degeneration or disruption of an intervertebral disc and intervertebral disc herniation. These and other pathologies of the spine are often treated with implants that can restore vertebral column height, immobilize or fuse adjacent vertebral bones, or function to provide flexibility and restore natural movement of the spinal column. Accordingly, different defects in the spinal column require different types of treatment, and the location and anatomy of the spine that requires corrective surgical procedures determines whether an immobilizing implantable device or a flexible implantable device is used for such treatment.

In a typical spinal corrective procedure involving distraction of tissue layers, damaged spinal tissue is removed or relocated prior to distraction. After the damaged tissue has been removed or relocated, adjacent spinal tissue layers, such as adjacent bone structures, are then distracted to separate and restore the proper distance between the adjacent tissue layers. Once the tissue layers have been separated by the proper distance, an immobilizing or flexible device, depending on the desired treatment, is implanted between the tissue layers. In the past, the implantable treatment devices have been relatively large cage-like devices that require invasive surgical techniques which require relative large incisions into the human spine. Such invasive surgical techniques often disrupt and disturb tissue surrounding the surgical site to the detriment of the patient.

Therefore, there remains a need for implantable treatment devices and methods that utilize minimally invasive procedures.

Such methods and devices may be particularly needed in the area of intervertebral or disc treatment. The intervertebral disc is divided into two distinct regions: the nucleus pulposus and the annulus fibrosus. The nucleus lies at the center of the disc and is surrounded and contained by the annulus. The annulus contains collagen fibers that form concentric lamellae that surround the nucleus and insert into the endplates of the adjacent vertebral bodies to form a reinforced structure. Cartilaginous endplates are located at the interface between the disc and the adjacent vertebral bodies.

The intervertebral disc is the largest avascular structure in the body. The cells of the disc receive nutrients and expel waste by diffusion through the adjacent vascularized endplates. The hygroscopic nature of the proteoglycan matrix secreted by cells of the nucleus operates to generate high intra-nuclear pressure. As the water content in the disc increases, the intra-nuclear pressure increases and the nucleus swells to increase the height of the disc. This swelling places the fibers of the annulus in tension. A normal disc has a height of about 10-15 mm.

There are many causes of disruption or degeneration of the intervertebral disc that can be generally categorized as mechanical, genetic and biochemical. Mechanical damage includes herniation in which a portion of the nucleus pulposus projects through a fissure or tear in the annulus fibrosus. Genetic and biochemical causes can result in changes in the extracellular matrix pattern of the disc and a decrease in biosynthesis of extracellular matrix components by the cells of the disc. Degeneration is a progressive process that usually begins with a decrease in the ability of the extracellular matrix in the central nucleus pulposus to bind water due to reduced proteoglycan content. With a loss of water content, the nucleus becomes desiccated resulting in a decrease in internal disc hydraulic pressure, and ultimately to a loss of disc height. This loss of disc height can cause the annulus to buckle with non-tensile loading and the annular lamellae to delaminate, resulting in annular fissures. Herniation may then occur as rupture leads to protrusion of the nucleus.

Proper disc height is necessary to ensure proper functionality of the intervertebral disc and spinal column. The disc serves several functions, although its primary function is to facilitate mobility of the spine. In addition, the disc provides for load bearing, load transfer and shock absorption between vertebral levels. The weight of the person generates a compressive load on the discs, but this load is not uniform during typical bending movements. During forward flexion, the posterior annular fibers are stretched while the anterior fibers are compressed. In addition, a translocation of the nucleus occurs as the center of gravity of the nucleus shifts away from the center and towards the extended side.

Changes in disc height can have both local and global effects. Decreased disc height results in increased pressure in the nucleus, which can lead to a decrease in cell matrix synthesis and an increase in cell necrosis and apoptosis. In addition, increases in intra-discal pressure create an unfavorable environment for fluid transfer into the disc, which can cause a further decrease in disc height.

Decreased disc height also results in significant changes in the global mechanical stability of the spine. With decreasing height of the disc, the facet joints bear increasing loads and may undergo hypertrophy and degeneration, and may even act as a source of pain over time. Decreased stiffness of the spinal column and increased range of motion resulting from loss of disc height can lead to further instability of the spine, as well as back pain.

Radicular pain may result from a decrease in foraminal volume caused by decreased disc height. Specifically, as disc height decreases, the volume of the foraminal canal, through which the spinal nerve roots pass, decreases. This decrease may lead to spinal nerve impingement, with associated radiating pain and dysfunction.

Finally, adjacent segment loading increases as the disc height decreases at a given level. The discs that must bear additional loading are now susceptible to accelerated degeneration and compromise, which may eventually propagate along the destabilized spinal column.

In spite of all of these detriments that accompany decreases in disc height, where the change in disc height is gradual many of the ill effects may be "tolerable" to the spine and patient and may allow time for the spinal system to adapt to the gradual changes. However, the sudden decrease in disc volume caused by the surgical removal of the disc or disc nucleus may increase the local and global problems noted above.

Many disc defects are treated through a surgical procedure, such as a discectomy in which the nucleus pulposus material is removed. During a total discectomy, a substantial amount (and usually all) of the volume of the nucleus pulposus is removed and immediate loss of disc height and volume can result. Even with a partial discectomy, loss of disc height can ensue. Discectomy alone is the most common spinal surgical treatment, frequently used to treat radicular pain resulting from nerve impingement by disc bulge or disc fragments contacting the spinal neural structures.

The discectomy may be followed by an implant procedure in which a prosthesis is introduced into the cavity left in the disc space when the nucleus material is removed. Thus far, the most common prosthesis is a mechanical device or a "cage" that is sized to restore the proper disc height and is configured for fixation between adjacent vertebrae. These mechanical solutions take on a variety of forms, including solid kidney-shaped implants, hollow blocks filled with bone growth material, push-in implants and threaded cylindrical cages.

A challenge in the use of a posterior procedure to install spinal prosthesis devices is that a device large enough to contact the end plates and expand the space between the end plates of the same or adjacent vertebra must be inserted through a limited space. In the case of procedures to increasing intervertebral spacing, the difficulties are further increased by the presence of posterior osteophytes, which may cause "fish mouthing" or concavity of the posterior end plates and result in very limited access to the disc. A further challenge in degenerative disc spaces is the tendency of the disc space to assume a lenticular shape, which requires a relatively larger implant than often is easily introduced without causing trauma to the nerve roots. The size of rigid devices that may safely be introduced into the disc space is thereby limited.

While cages of the prior art have been generally successful in promoting fusion and approximating proper disc height, typically these cages have been inserted from the posterior approach, and are therefore limited in size by the interval between the nerve roots. Further, it is generally difficult to implant from the posterior approach a cage that accounts for the natural lordotic curve of the lumber spine.

It is desirable to reduce potential trauma to the nerve roots and yet still allow restoration or maintenance of disc space height in procedures involving vertebrae fusion devices and disc replacement, containment of the nucleus of the disc or prevention of herniation of the nucleus of the disc. In general, minimally invasive surgical techniques reduce surgical trauma, blood loss and pain. Exemplary minimally invasive intervertebral fusion devices and surgical techniques include those described in U.S. Pat. Nos. 5,571,189 and 5,549,679 to Kuslich and embodied in the XLIF® procedure of NuVasive, Inc. of San Diego, Calif.

However, all minimally invasive fusion devices still require a surgical access opening that is as large as the device to be implanted. Generally speaking, the access aperture in minimally invasive procedures is at least 15-30 mm in diameter or length. Also, because minimally invasive procedures require direct visualization, the surgeon may need to cut bone and must significantly retract soft tissues and the nerve root, potentially causing nerve root injury or persistent post-operative pain.

By contrast, percutaneous surgery is done using x-ray visualization and image guidance and as such does not require resection of bony or soft tissue for direct visualization of the disc. Further, the incision is generally in the range of about 10 mm, much smaller than the access aperture in MIS procedures. Thus, percutaneous surgery results in a dramatic reduction in morbidity rates and more rapid recovery, both of which leading to significantly shorter hospitalization times.

Exemplary percutaneous methods of fusing the lumbosacral region of the spine from an axial approach are described in U.S. Pat. No. 6,558,383 to Cunningham et al. and U.S. Pat. No. 7,087,058 to Cragg, which are incorporated herein by reference. The method and system described in U.S. Pat. No. 7,087,058 are limited to fusing either the L5-SI or the L4-L5-SI motion segments using a rigid device and are further limited to an axial approach. Further, although U.S. Pat. No. 7,087,058 describes the method as being percutaneous, the method still requires an access opening of at least 22 mm to accommodate the implant. The larger a surgical exposure is, the greater the likelihood of attendant bleeding and injury to local muscular, ligamentous, vascular, and nervous tissues and in the lumbar region, while the bowels may also be damaged.

U.S. Pat. No. 9,566,170 to Schell et al. describes a method and system for percutaneous fusion to correct disc compression involving several steps such as inserting percutaneously an implant with facet or posterior fixation. Such system may include an implant, an elongated cannulated insertion tool and elongated lock shaft positioned within the insertion tool.

It would be advantageous to provide a system and method that would more easily, more effectively, and/or more safely treat the degenerative disc disease of hundreds of thousands of suffering individuals. It would also be advantageous to provide a system and method of performing a true percutaneous interbody fusion at all levels of the spine.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a minimal impact access system for accessing the vertebral disc space is provided. The system includes a pad configured to be secured to a skin surface of a patient and defining an opening. A retractor frame is secured with respect to the pad and defines an opening at least partially aligned with the opening of the pad. A swivel base is secured with respect to the pad and includes a swivel at least partially aligned with the openings of the pad and retractor frame. An outermost dilating tube is received by the swivel for pivotal movement with respect to the pad, and defines a corridor for accessing the vertebral disc space of the patient.

In another aspect, an alternative embodiment of a minimal impact access system provides an alternative to the skin-based design. Such an alternative system may include a holding arm assembly having one portion that attaches to a dilating tube to hold it in place while another portion of the holding arm assembly may be fixed to a modified pedicle tap on the contralateral side. As such, the contralateral pedicles may be tapped, with a specially designed tap having a removable shaft that may be removed to leave a shortened distal portion anchored in the nearest contralateral (i.e. opposite the side of the dilating tube) pedicle. This configuration may be referred as a pedicle-based retractor arm.

It should be understood that these types of minimal impact access systems are not limited to applications in which the vertebral disc space is accessed, but could also be used to provide minimally invasive access to other locations, including the retroperitoneal space, intraperitoneal space, or intrathoracic space for spinal and non-spinal surgical procedures.

DESCRIPTION OF THE ILLUSTRATED EMBODIMENTS

Figure 1:
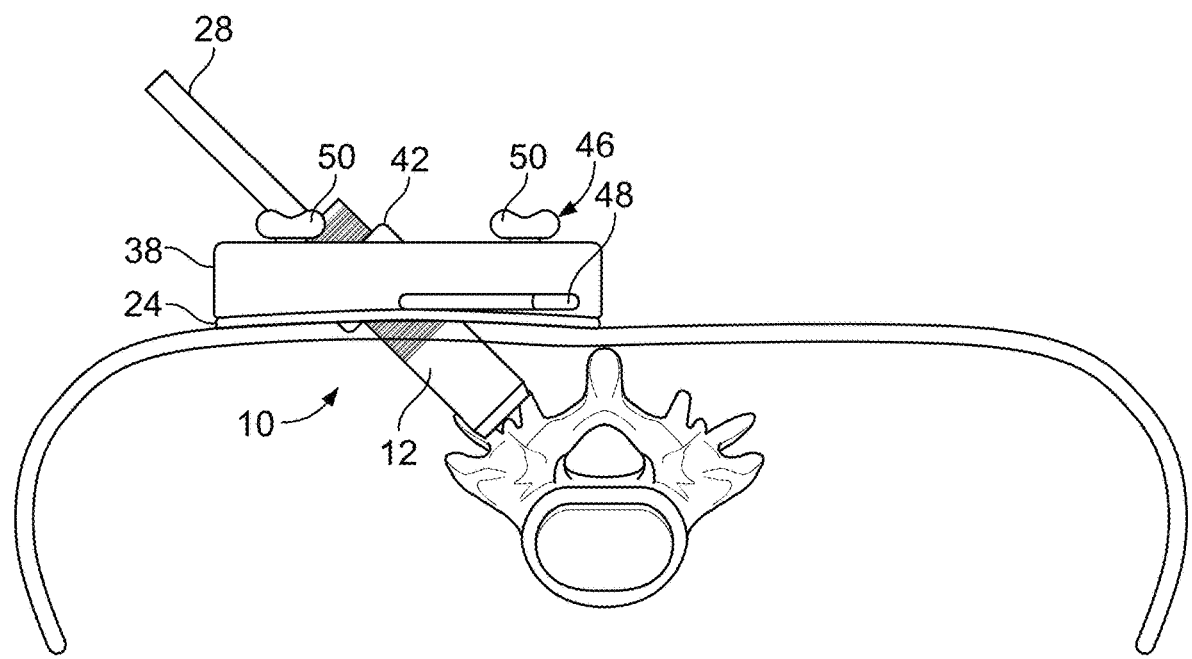
FIG. 1 is a schematic axial view of a system according to the present disclosure in position with respect to the spine.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The clinical and radiographic benefits of lumbar interbody fusion have been well described in the literature and include both direct and indirect decompression of the neural elements, as well as a high rate of bony fusion. A number of approaches have been described to achieve interbody fusion of the lumbar spine (posterior, anterior, and lateral), each with a unique set or advantages and challenges. In an effort to minimize the challenges and maximize the benefits of the posterior interbody approach, the present disclosure provides a superior articular facet interbody reconstruction (which may be referred to herein as "SAFIR") procedure for lumbar interbody fusion. The present disclosure also provides an alternative approach (shown in FIGS. 34-37) without any bone removal. In such an embodiment, the initial anchor is placed directly into the disc space via fluoroscopy or spinal navigation or direct visualization or the like to assist in safe and accurate placement, with the particular approach depending on the technology available, unique patient anatomic features, and/or surgeon preference.

The current disclosure generally relates to apparatus and methods for accessing a vertebral disc space in a less minimally invasive procedure and to improve on the drawbacks of more open surgery. More particularly, the present disclosure focuses on far-lateral transforaminal access with a skin-based fixation.

One aspect of the present disclosure relates to a fixation system that allows for complete and accurate position using positioning motions in the x-y directions, as well as a swivel for angular orientation.

Another aspect of the present disclosure relates to exact positioning over the facet joint and the ability to reposition the access angle without losing the in-sight target, as the final dilating tube is configured to anchor into either the cortical wall or the disc rim.

A third aspect of the present disclosure relates to the ability to use the same set-up for accessing the disc via Kambin's triangle for cases where appropriate, which is between the nerve roots and with no bony removal.

Another aspect of the present disclosure relates to a method of carrying out the minimally invasive by positioning the access system and creating the access to the disc space via a partial facetectomy, such as the SAFIR approach.

Yet another aspect of the present disclosure relates to tools that are advanced through dilating tubes to split the facet joint and provide anchor and removal of the superior articular portion of the facet to gain access to the disc.

An additional aspect of the present disclosure relates to a pedicle-based retractor system in which a holding arm assembly is attached to a temporary pedicle-based tap.

These and others aspects of the present disclosure will be apparent from the following description.

First Exemplary System

FIGS. 1-33 illustrate an exemplary system and minimally invasive surgical (MIS) method for accessing a vertebral disc space with the minimum tissue and bone distraction/removal. The system described herein may be used in a standalone manner with skin-mount capability (i.e., without any attachment to the support table) and allow for access to the disc space. In another embodiment, which is illustrated in FIGS. 34-37 and which will be described in greater detail, pedicle-based mounting is employed instead of skin-mounting. Regardless of the particular mounting approach, once the disc space has been accessed, it may be sized, followed by the cutting, disruption, and removal of disc material. When the disc material has been removed from the disc space, an implant may be deployed into the disc space, followed by the insertion of bone graft material and closure of the site.

FIG. 1 shows a skin-based mounting device or system 10 according to an aspect of the present disclosure, which can hold a set of distraction or dilation tubes at an adjustable angle to access the disc space in an extra-foraminal trajectory. One of the distracting or dilating tubes 12 (which is referred to herein as the final or outermost dilating tube) is visible in FIG. 1, while additional distracting or dilating tubes 14-22 (which are referred to herein as preliminary or inner dilating tubes) are visible in FIGS. 4A-4F and will be described in greater detail herein.

Figure 2:
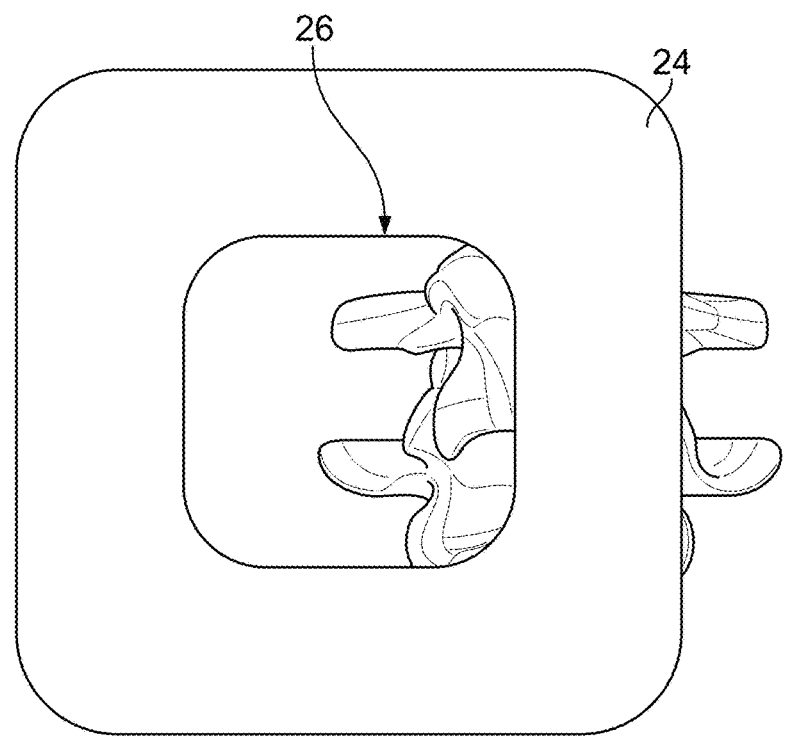
FIG. 2 is a back view of the location of a gel pad with respect to the spine.

FIG. 2 shows a skin-based gel pad 24 of the system 10 of FIG. 1. The gel pad 24 may be made out of soft and flexible material, with an adhesive backing protected by a peel-away sheet (not shown) to be removed prior to usage. The gel pad 24 defines a central opening or middle cut-out 26 to accommodate the outermost dilating tube 12 with room for x-y translation motions (in a plane defined by the pad 24) in order to optimize the best trajectory based on anatomical differences.

Figure 3A:
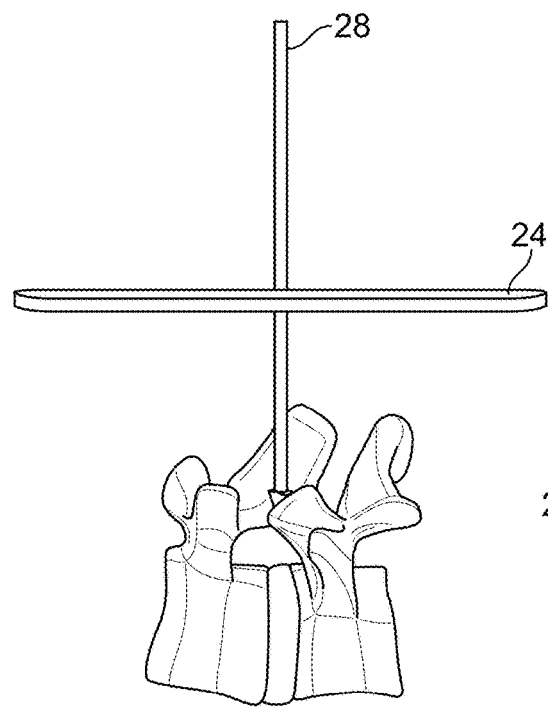
FIG. 3A is a lateral view showing a spine segment with a targeting osteotome in place for optimizing the access location and trajectory during an exemplary procedure.
Figure 3B:
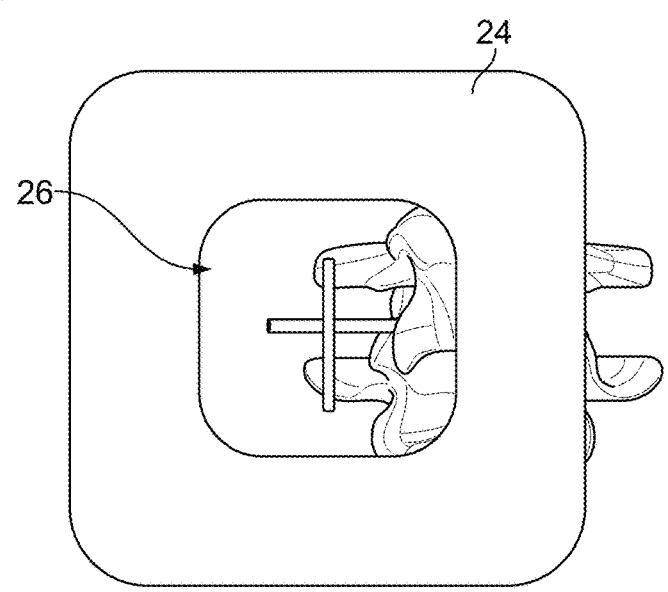
FIG. 3B is a back view showing the targeted access location of FIG. 3A through a window of the gel pad.
Figure 3C:
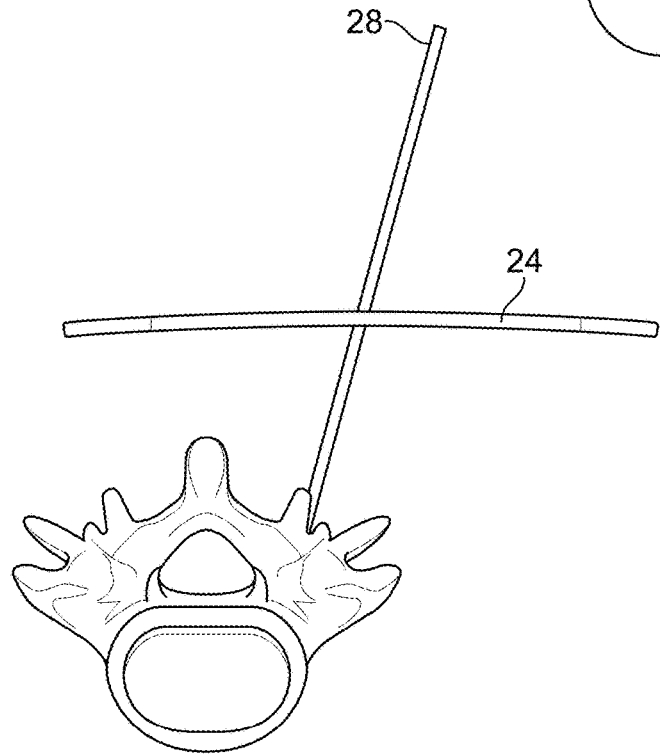
FIG. 3C is an axial view of the targeted access location of FIG. 3A.

The dilating tubes 12-22 are moved into position by sliding or advancing them over an elongated guide 28, which may be variously configured. For example, FIGS. 3A-3E illustrate an approach whereby an elongated guide 28 configured as a dedicated osteotome with a spade-like tip 30 (FIGS. 3D and 3E) may be used to target an access location in a facet joint. In FIG. 3A, a lateral view of a spine segment can be seen with the elongated guide 28 in place. In FIG. 3B, an in-line view of the targeting position is shown, while FIG. 3C is an axial view of that position.

Figures 3D, 3E, 3F:
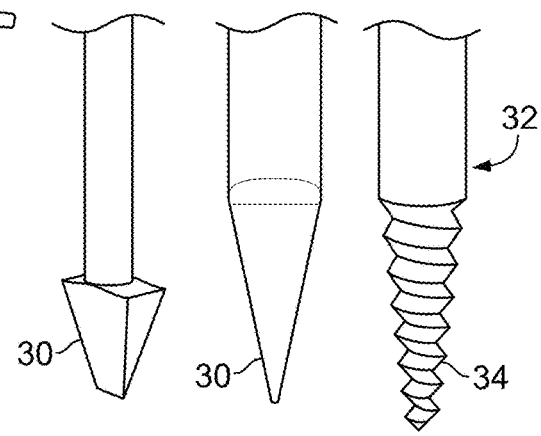
FIG. 3D is an orthogonal view of the tip of the access osteotome of FIG. 3A.
FIG. 3E is a lateral view of the tip of the targeting osteotome of FIG. 3A.
FIG. 3F is a lateral view of a threaded tip of a metallic pin.

FIG. 3F illustrates an alternative embodiment of an elongated guide, which alternative can serve as an anchor point and provide a guide for the passage of the various dilating tubes 12-22. In particular, FIG. 3F shows a portion of a metallic pin 32 with a threaded distal tip 34 that can be drilled into the superficial aspect of the joint line or directly into the disc (identified at "D" in FIG. 33 for an approach via Kambin's triangle "T"), based on the particular approach. Another possible modification to the anchor or guide would be a version of the anchor or guide that has an EMG (electromyographic) stimulation tip that is directional and permits localization of the exiting nerve root "E" to prevent inadvertent root injury.

Once the target location has been confirmed via fluoroscopy, a series of distracting or dilating tubes 12-22 (FIGS. 4A-4F) can be used to dilate or expand the tissue so that access to the site can be made. During this site access, one would ensure that no nerves are being compromised by doing neuro-monitoring of those particular nerves, as is known in the medical community. FIGS. 4A-4F show the step-by-step dilation process with the different tubes 12-22 sliding one over the previous one until the desired dilated size through the tissue is achieved. Each dilating tube has a diameter that is greater than the preceding dilating tube to allow for each dilating tube to be slid over the previously positioned dilating tube(s). While FIGS. 4A-4F show a series of six dilating tubes having increasingly large diameters from an innermost tube 14 (FIG. 4A) to a series of intermediate tubes 14-22 (FIGS. 4B-4E) to the outermost tube 12 (FIG. 4F), it is within the scope of the present disclosure for more or fewer than six dilating tubes to be used.

Figure 4A:
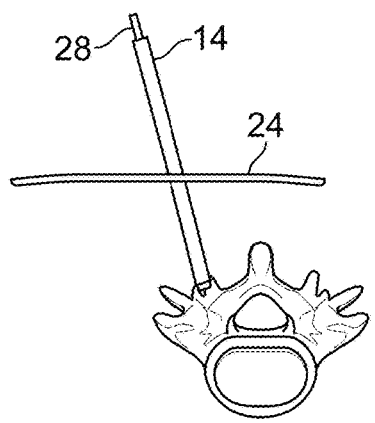
FIG. 4A is an axial view of a first dilating tube positioned over an elongated guide for dilating or expanding tissue to allow access to the disc space, with the gel pad omitted for clarity.
Figure 4B:
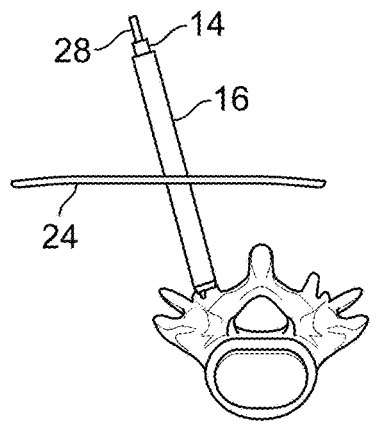
FIG. 4B is an axial view of a second dilating tube positioned over the first dilating tube of FIG. 4A.
Figure 4C:
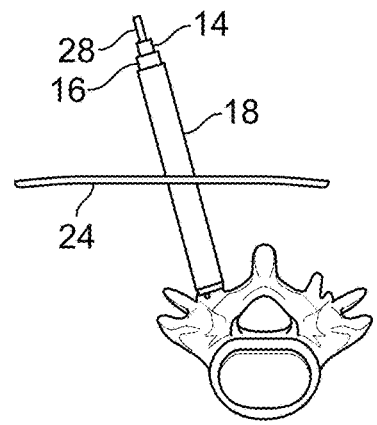
FIG. 4C is an axial view of a third dilating tube positioned over the second dilating tube of FIG. 4B.
Figure 4D:
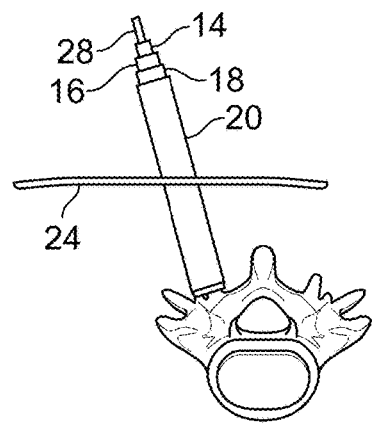
FIG. 4D is an axial view of a fourth dilating tube positioned over the third dilating tube of FIG. 4C.
Figure 4E:
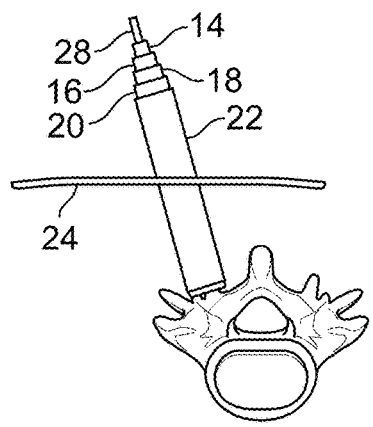
FIG. 4E is an axial view of a fifth dilating tube positioned over the fourth dilating tube of FIG. 4D.
Figure 4F:
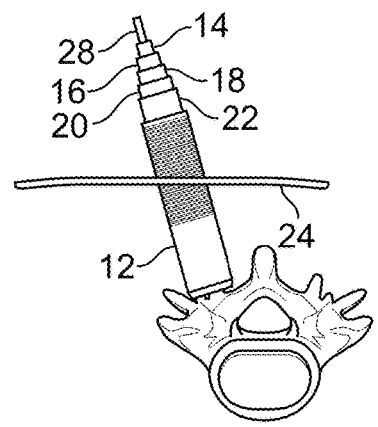
FIG. 4F is an axial view of a sixth dilating tube positioned over the fifth dilating tube of FIG. 4E.
Figure 4G:
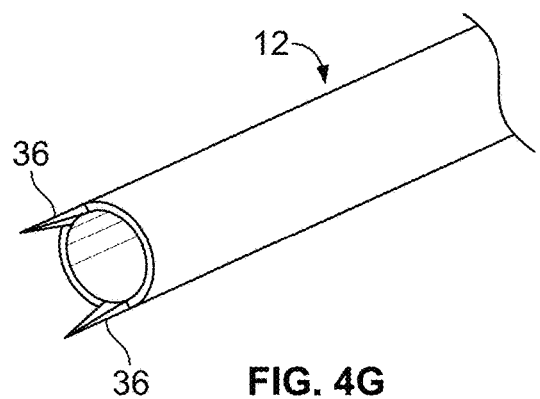
FIG. 4G is a perspective view of a distal portion of a dilating tube with anchoring spikes.

FIG. 4G illustrates an embodiment in which one of the dilating tubes, which may be the final or outermost dilating tube 12, has a front or distal end that includes at least one impaction tooth or anchoring spike 36. In one embodiment, two impaction teeth 36 are provided and oriented 180° apart (i.e., at 6 and 12 o'clock), with each being approximately 2-3 mm long. In other embodiments, a different number of impaction teeth may be provided and/or the various impaction teeth may be arranged in a different circular configuration at the front or distal end of the dilating tube. If provided, the impaction tooth or teeth 36 permit gentle impaction of the dilating tube 12 to provide more stable docking of the access system 10.

Figure 5:
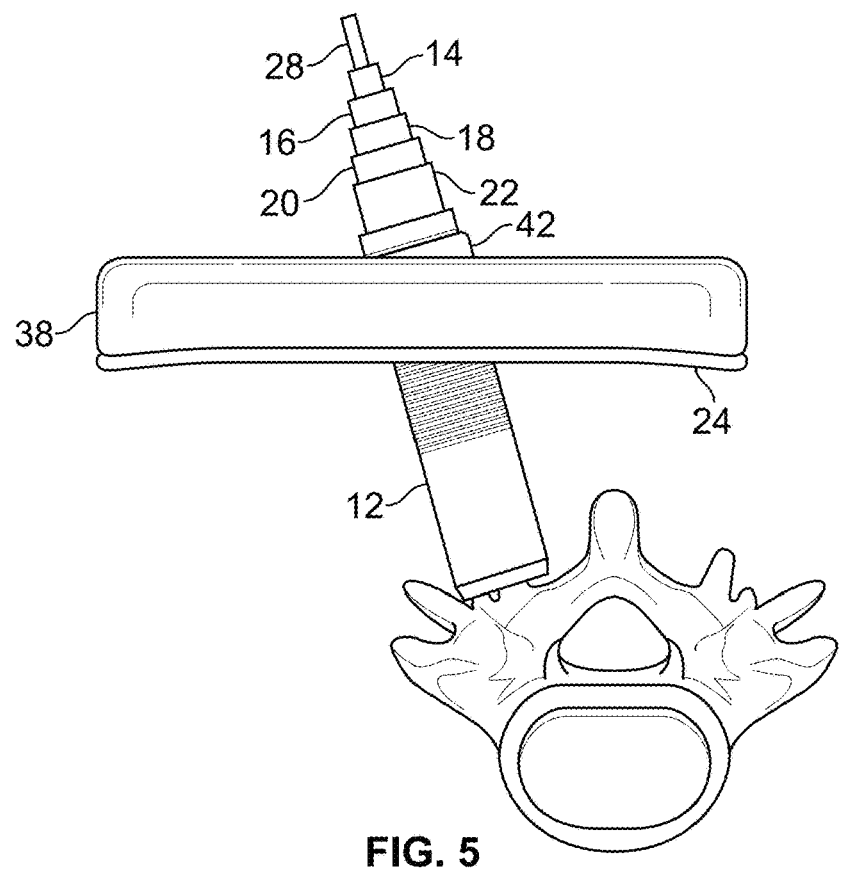
FIG. 5 is an axial view of the dilating tubes of FIGS. 4A-4F, the gel pad of FIG. 2, and a retractor frame in place with respect to the spine.

A retractor frame 38 can be safely positioned over the gel pad 24, with an opening 40 of the retractor frame 38 at least partially aligned with the opening 26 of the pad 24. So positioning the retractor frame 38 over the gel pad 24 also includes sliding a swivel 42 and associated swivel base 44 over the largest dilating tube 12, as shown in FIG. 5.

Figure 6:
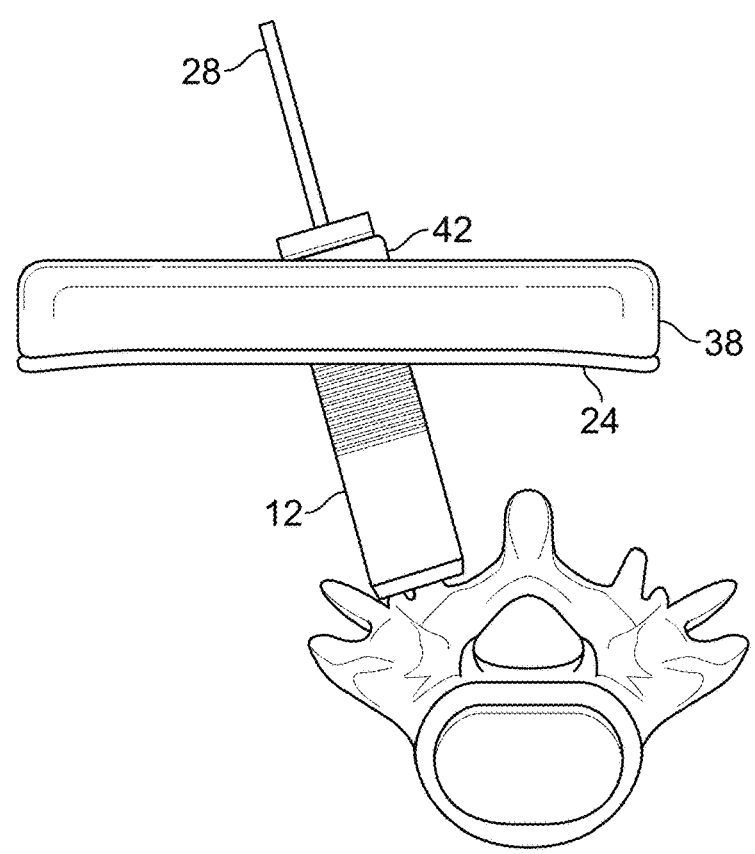
FIG. 6 is an axial view of the system and spinal section of FIG. 5, with the dilating tubes of FIGS. 4A-4E removed from the outermost dilating tube.
Figure 7:
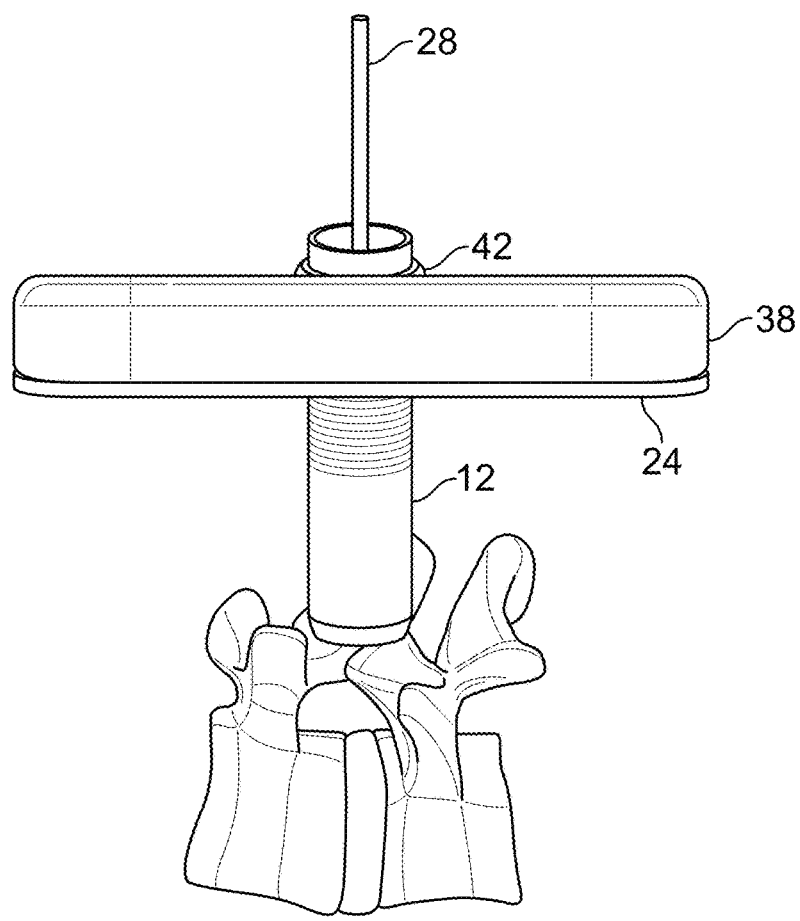
FIG. 7 is a lateral view of the system and spinal section of FIG. 6.
Figure 8:
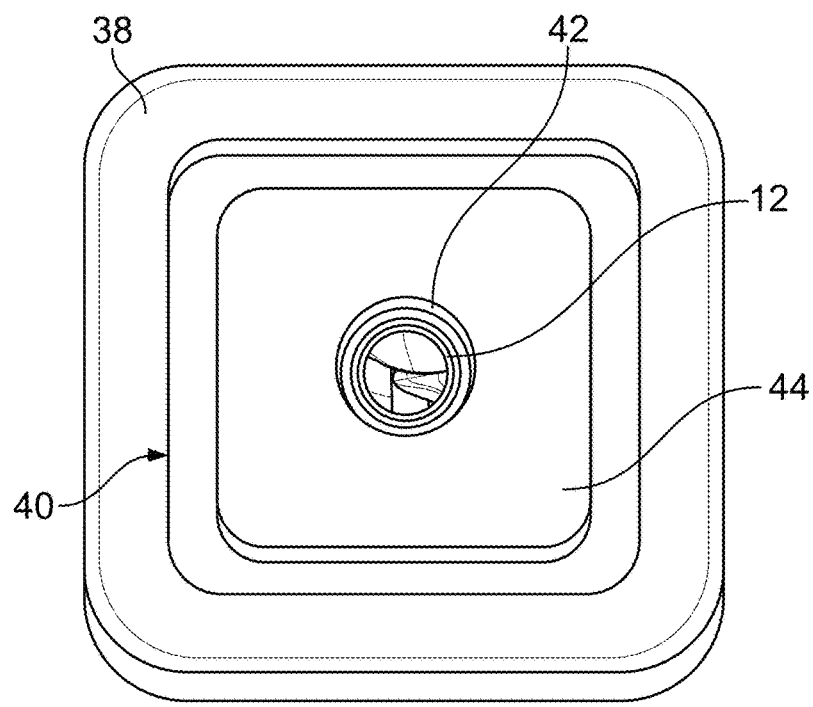
FIGS. 8-10 are in-line views of the system of FIGS. 6 and 7, in increasing proximity to the access location.
Figure 9:
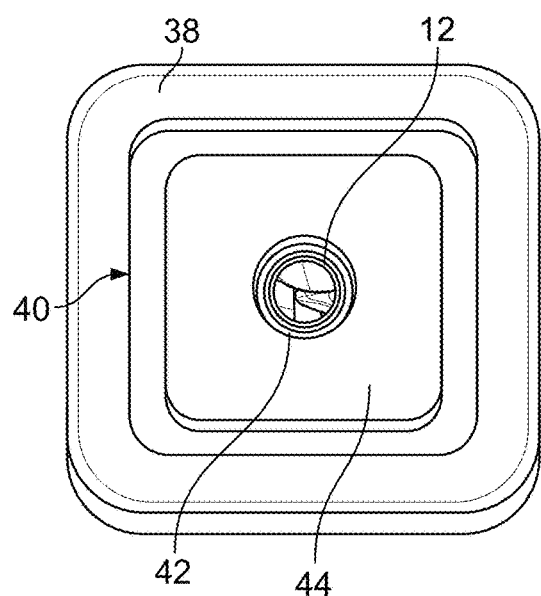
Figure 10:
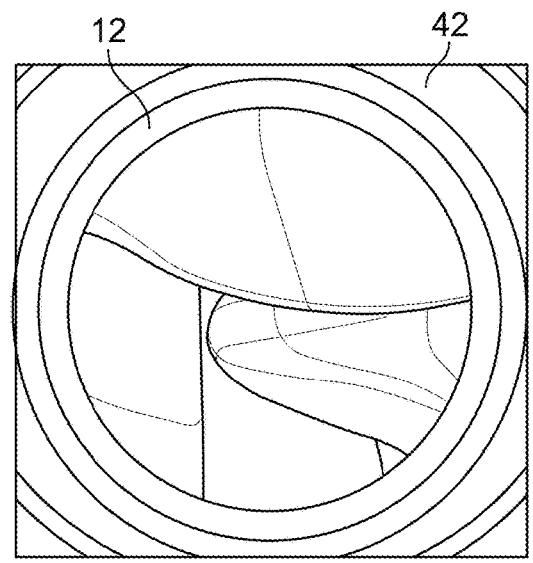

With the retractor frame 38 (including the swivel 42 and swivel base 44) in position, all of the inner dilating tubes 14-22 may be removed, with the outermost dilating tube 12 being left in place with the elongated guide 28, as shown in FIGS. 6 and 7. FIGS. 8-10 show the surgical site exposed following the tube dilation process under increasingly larger magnification with each view.

Figure 11:
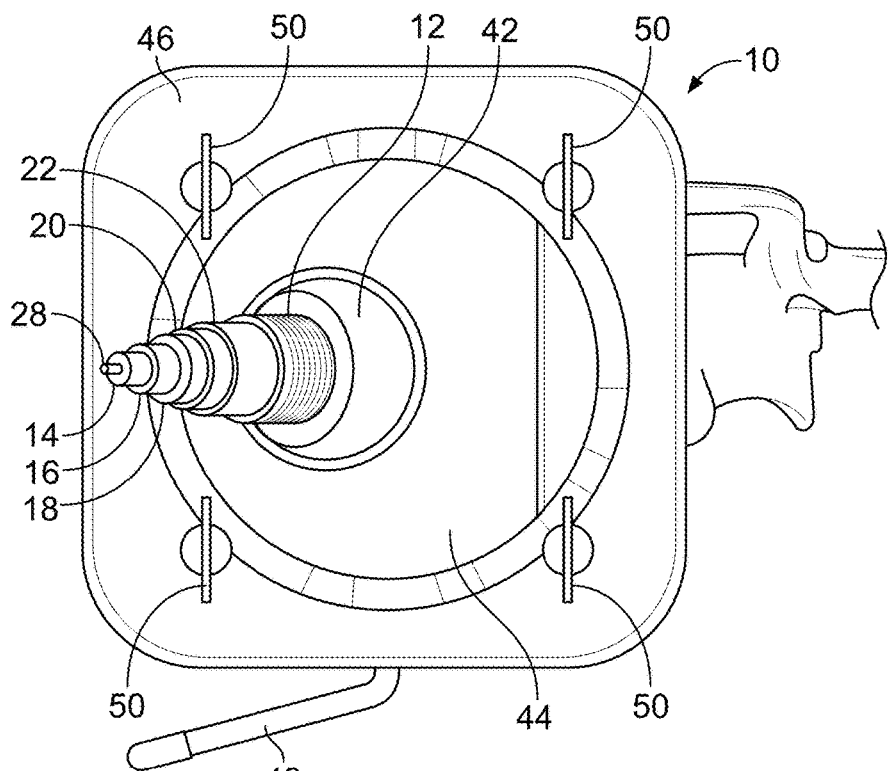
FIG. 11 is a top view of the system of FIGS. 5-10 and a locking plate in place with respect to the spine.
Figure 12:
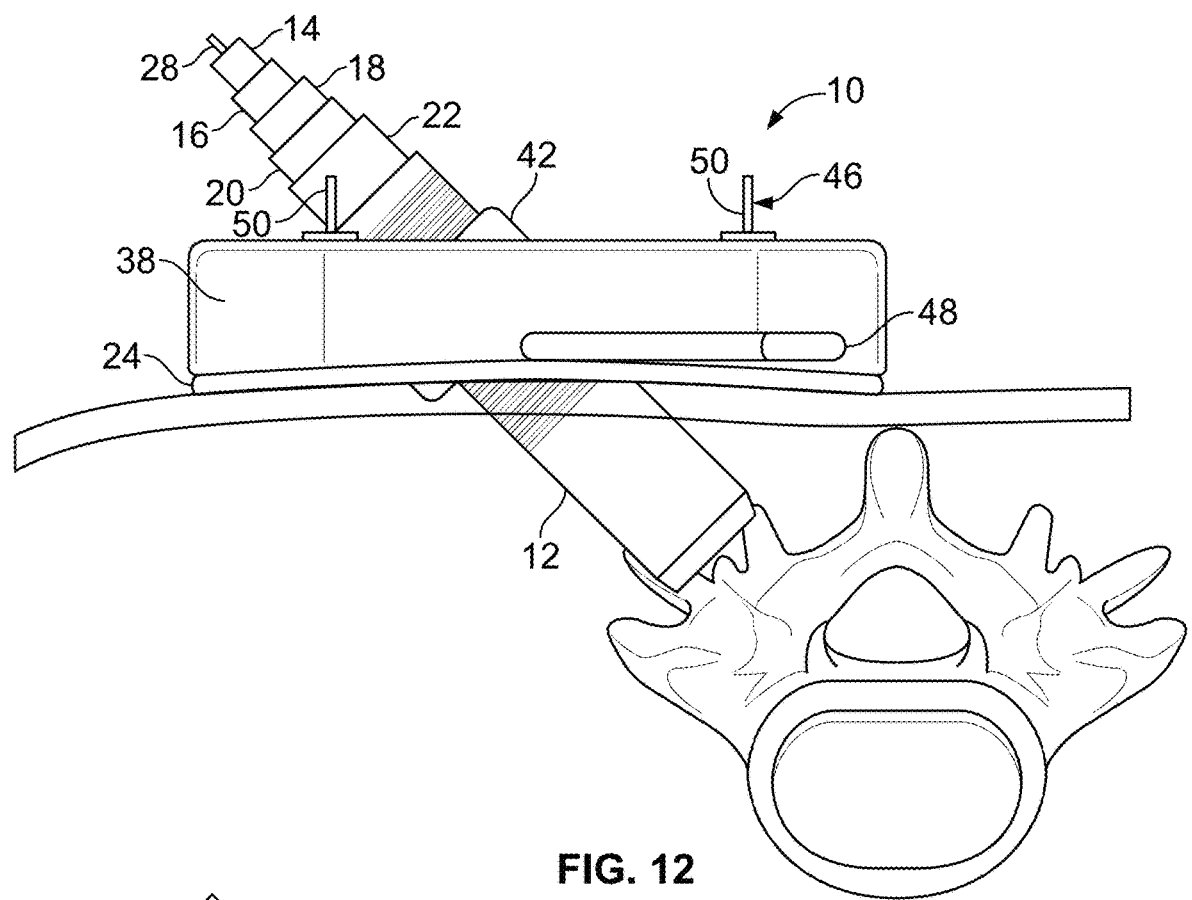
FIG. 12 is an axial view of the system of FIG. 11, showing the use of a lever for suction action.
Figure 13:
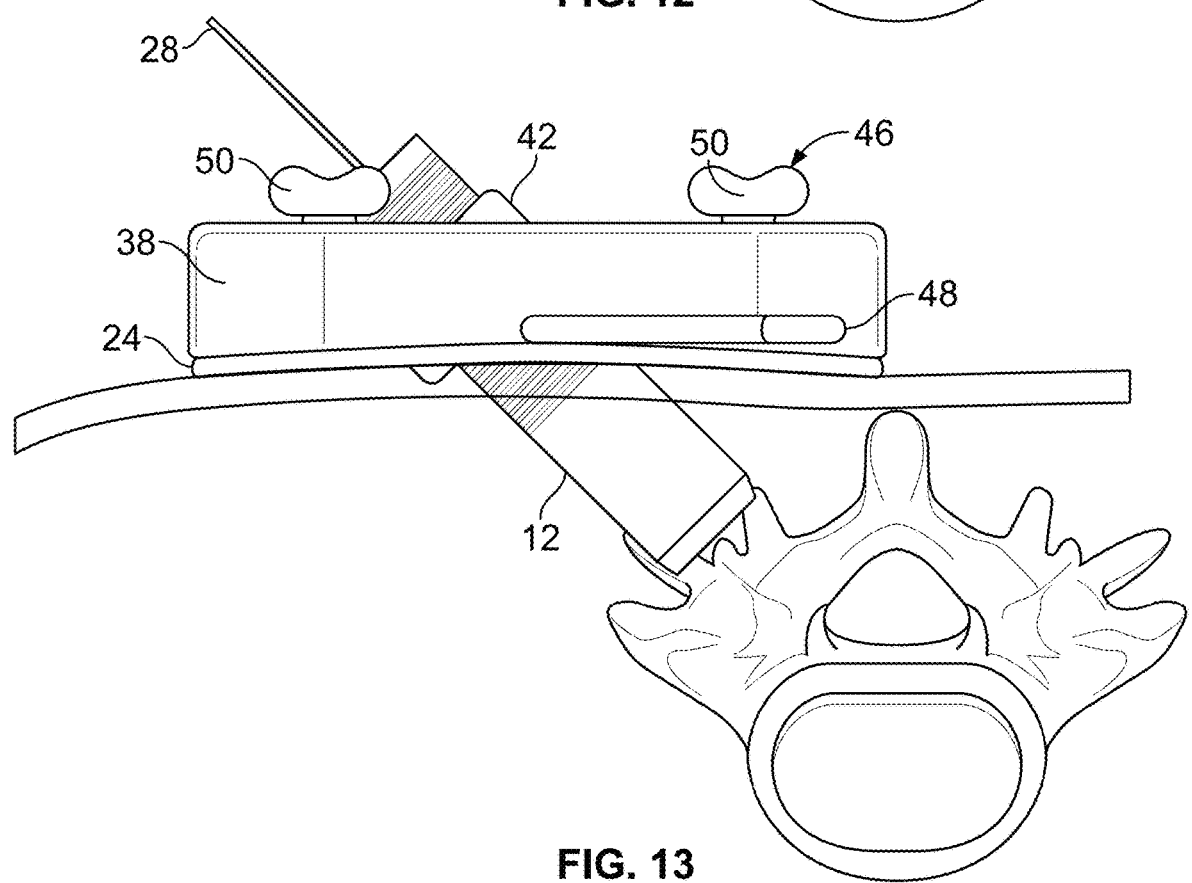
FIG. 13 is an axial view of the system of FIG. 11, showing tightening nuts of the locking plate being activated.

FIGS. 11 and 12 show the system 10 with the swivel base 44 mounted over the various dilating tubes 12-22 to provide a clamping mechanism of the associated swivel 42. A clamping ring plate 46 may be secured over the swivel base 44 to hold the system 10 together.

The retractor frame 38 is coupled or clamped to the gel pad 24. As shown in FIG. 12 (which shows the system 10 following the removal of the inner dilating tubes 14-22), a lever 48 of the retractor frame 38 may be activated to produce a sucking action similar to a suction cup between the gel pad 24 and the swivel base 44. The benefit of a sucking action is that it can be released and re-activated during manipulation of the outermost dilating tube 12 for a better view or approach of the surgical site. A mechanism, such as the wing nuts 50 shown in FIGS. 11-13, may provide a clamping force over the clamping ring plate 46 that, in turn, provides the holding force to secure the swivel base 44 that locks the outermost dilating tube 12 in place.

Figure 14:
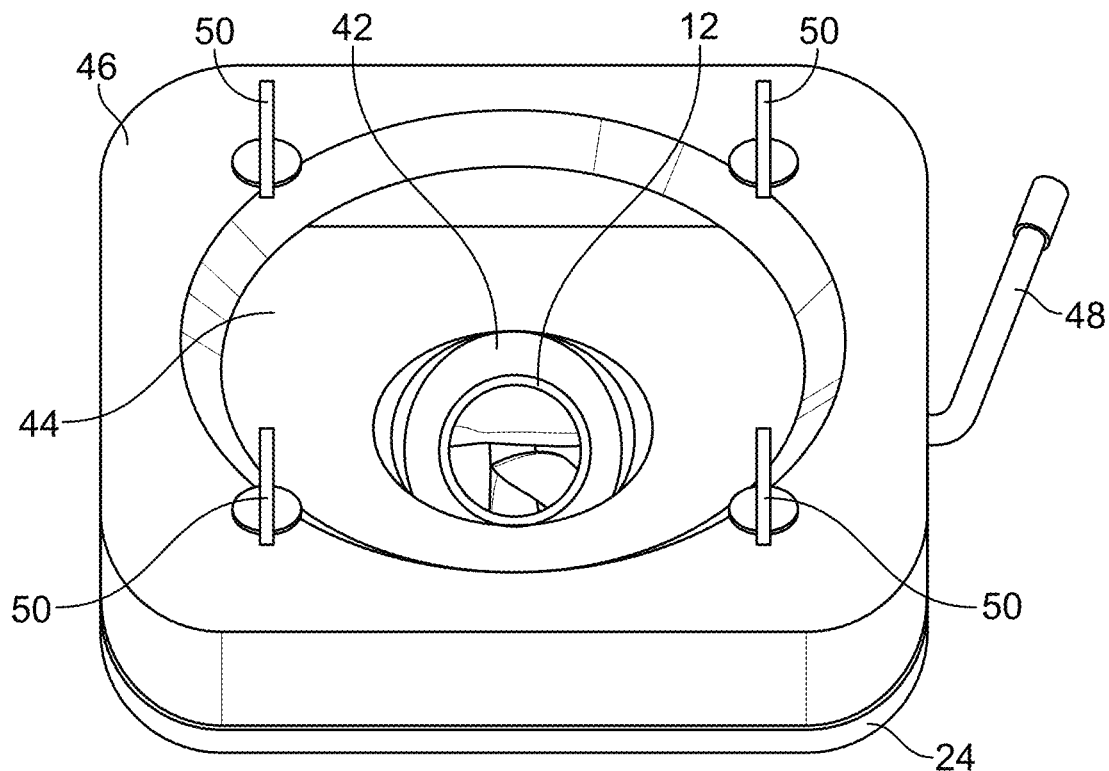
FIGS. 14 and 15 are in-line views of the system of FIG. 11, in increasing proximity to the access location.
Figure 15:
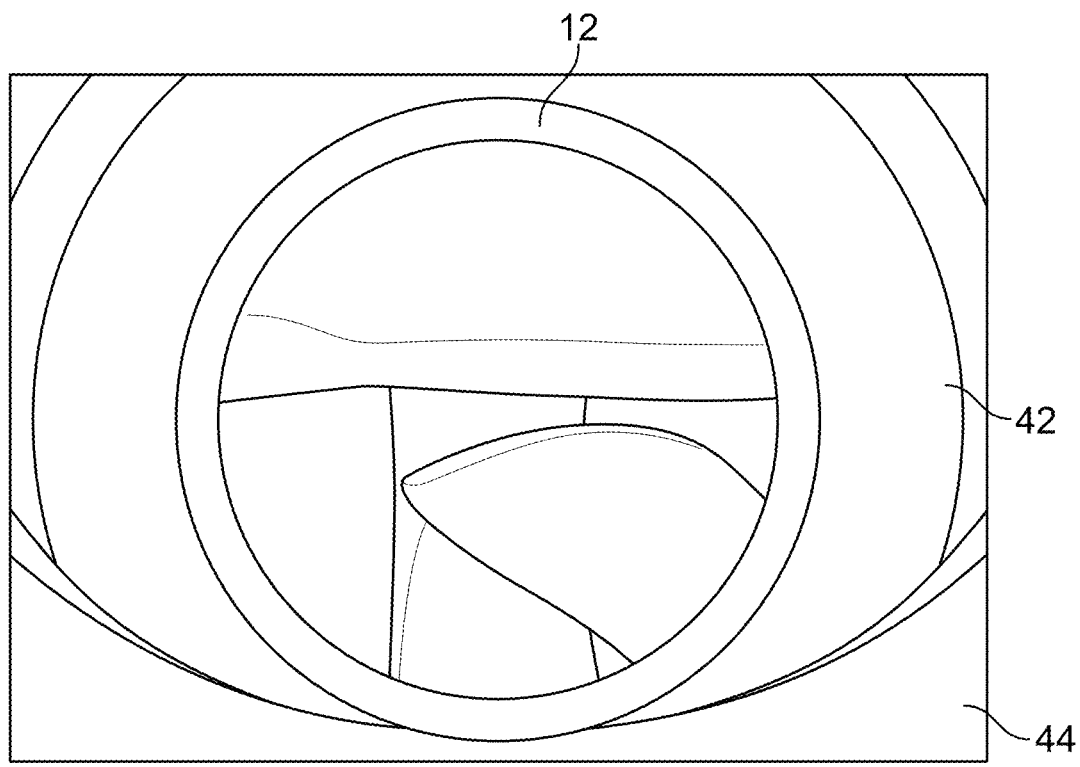
Figure 16:
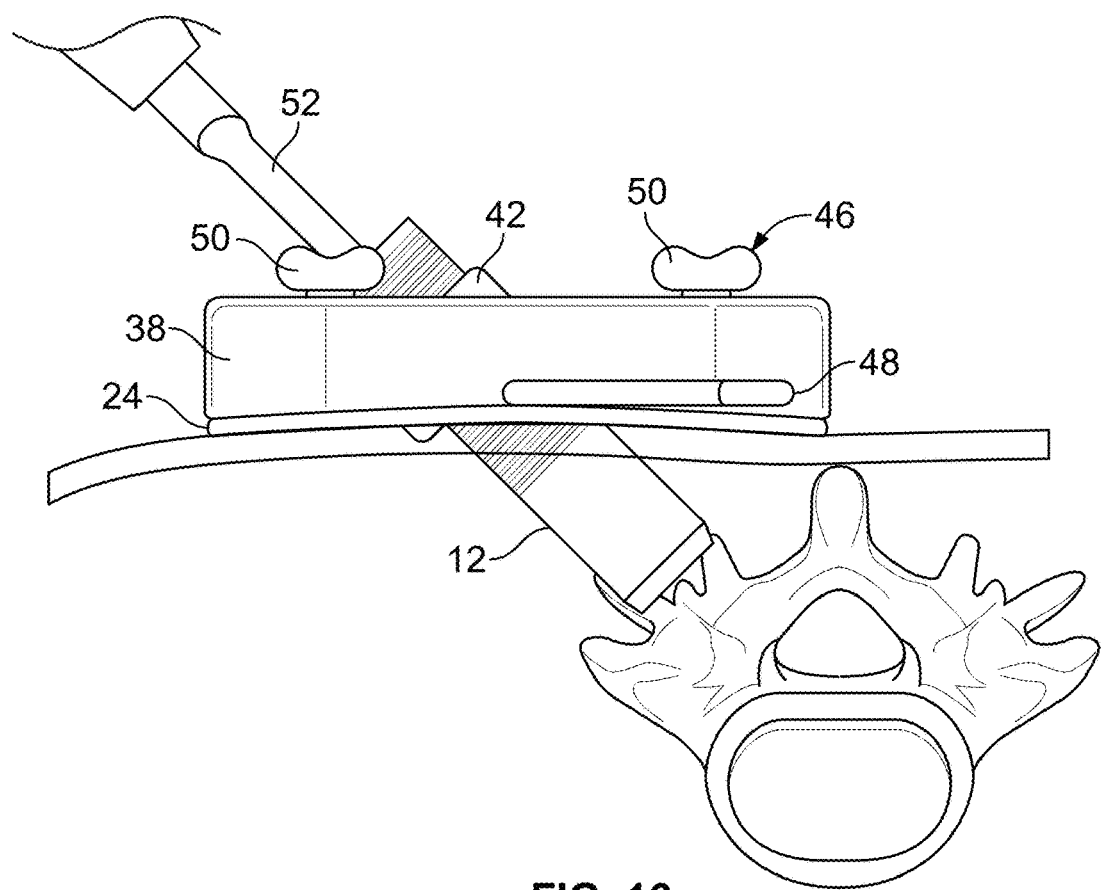
FIG. 16 is an axial view of the system of FIG. 11, showing a splitting osteotome being advanced through the dilating tube toward the access location of a facet joint.
Figure 17:
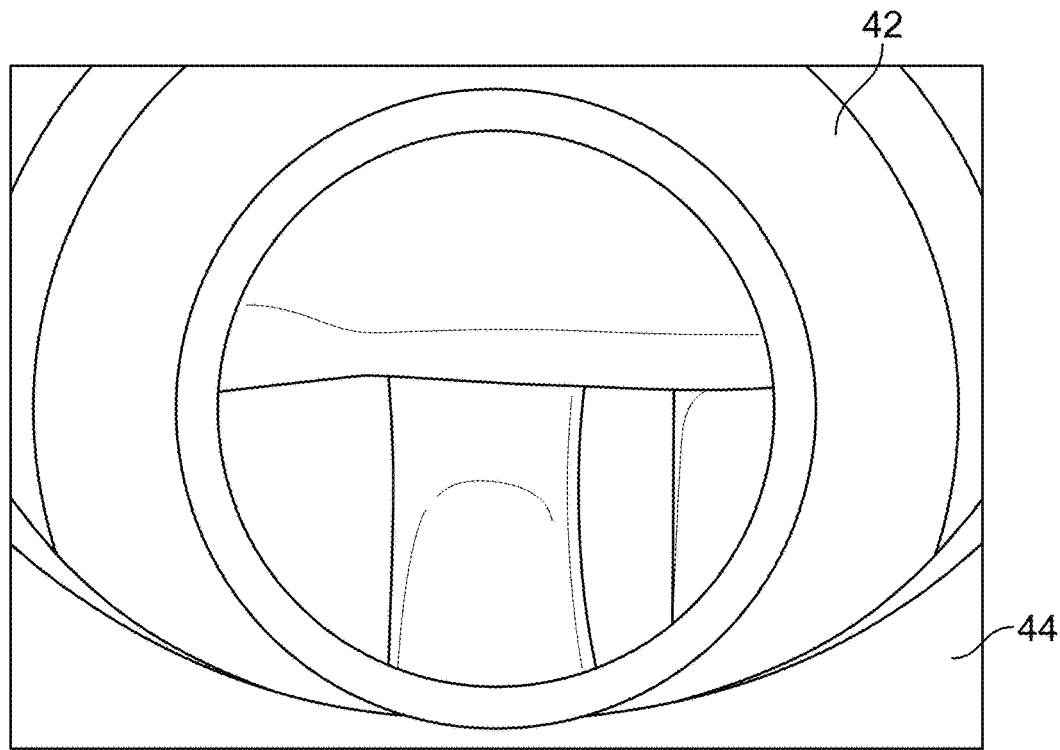
FIG. 17 is an in-line detail view of the separated facet joint, showing the adjacent inferior articular process and not the adjacent superior articular process.
Figure 18:
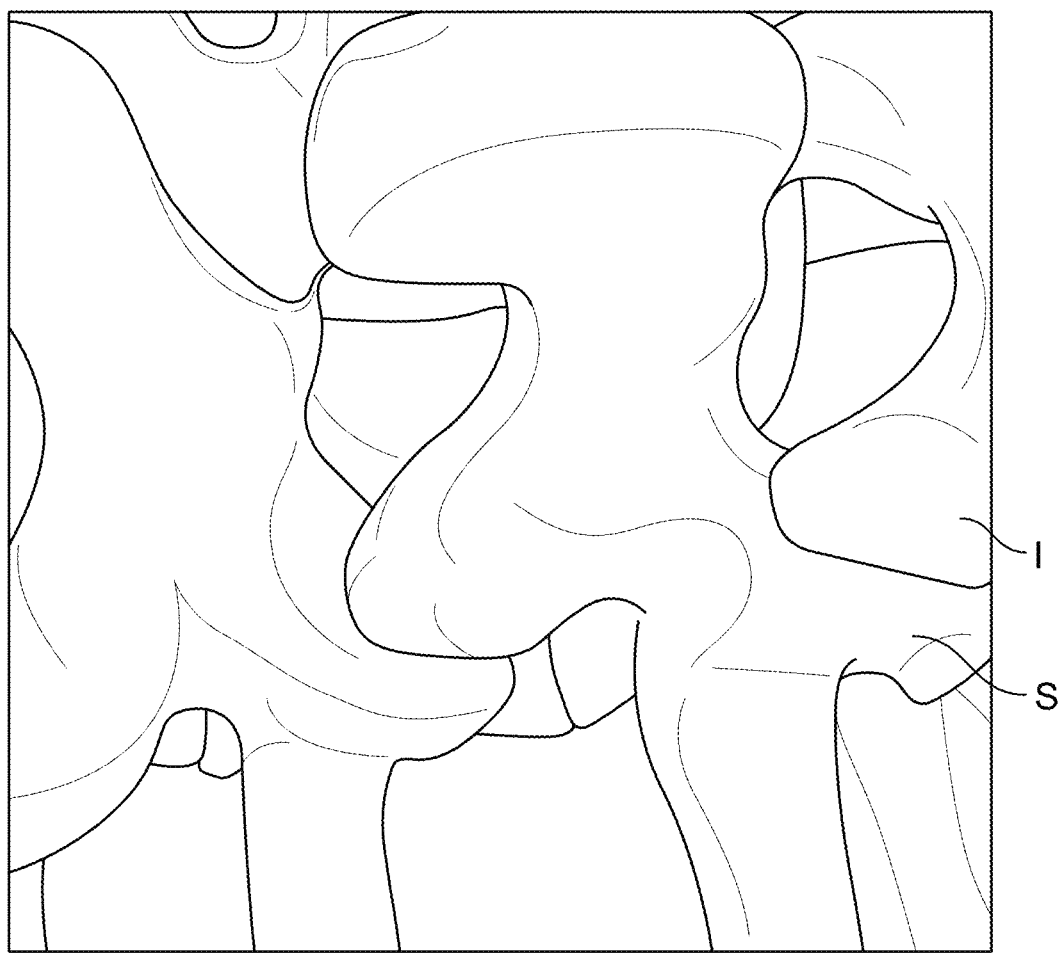
FIG. 18 illustrates the inferior and superior articular processes adjacent to the facet joint of FIG. 17.
Figure 19:
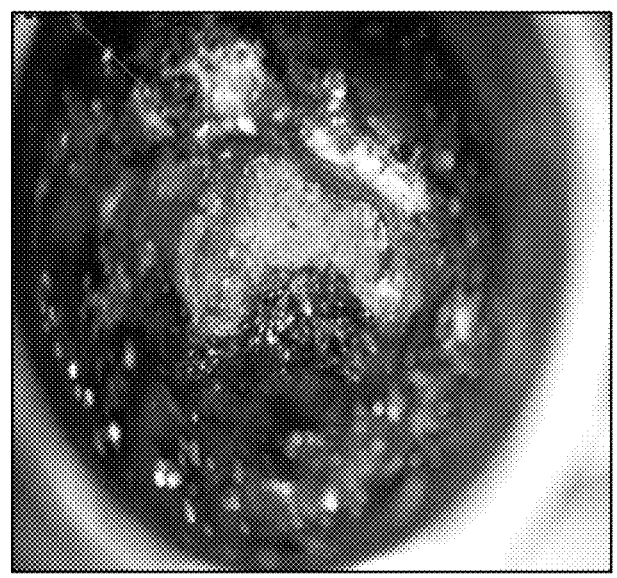
FIG. 19 is an in-line detail view of the separated facet joint, with a portion of the adjacent superior articular process having been removed.

FIG. 14 shows the surgeon's view of the surgical site, with a zoomed-in view being shown in FIG. 15, where the facet is plainly visible for manipulation following removal of the elongated guide 28. Such manipulation could be to use a splitting osteotome 52 to break the facet joint, as shown in FIG. 16. FIG. 17 shows the results of a partially cut facet joint with only the inferior anterior process remaining, following the removal of a portion of the superior anterior process. In order to better understand the approach and the goal of this surgical approach, one can see in FIG. 18 the facet with the inferior articular process "I" and the superior articular process "S" intact, while FIG. 19 is another illustration of the surgical site with a portion of the superior articular process "S" already having been removed.

Associated Devices

Figure 20:
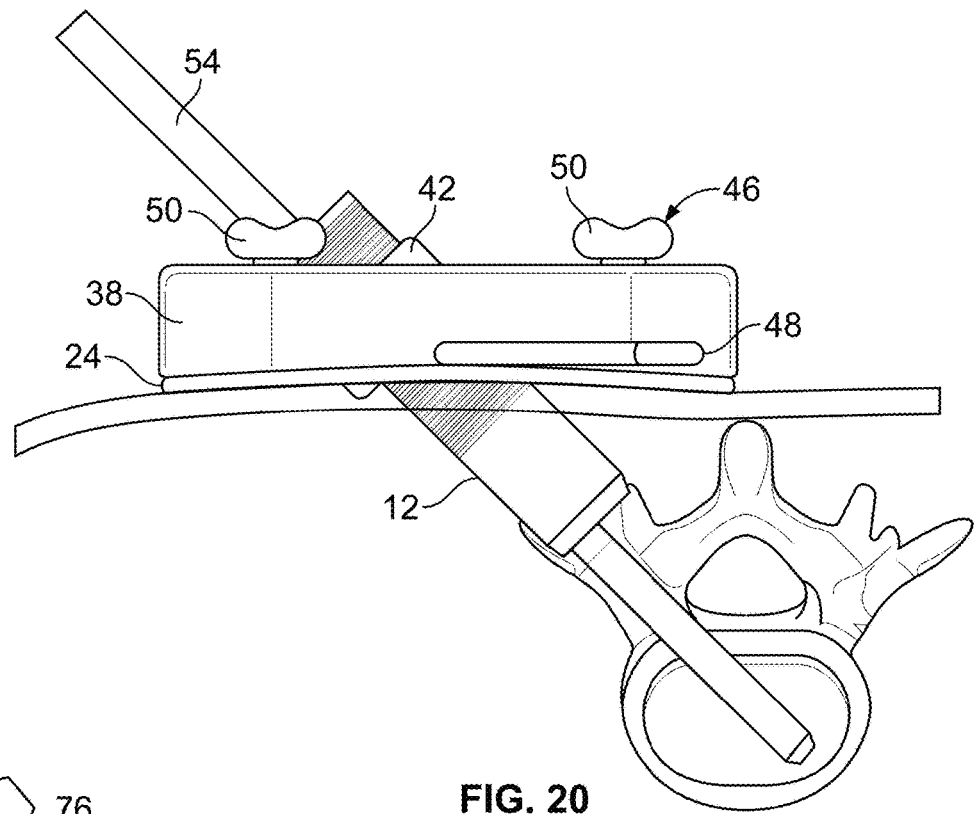
FIG. 20 is an axial view of the system of FIG. 11, showing a shaver tool accessing the disc space.

Following the removal of a portion of the facet, access to the disc is straightforward and a series of tools, such as a shaver tool 54 of the type shown in FIG. 20, can be used to clear out the nucleus material from the disc. Other instruments can be used for that purpose, and each pass of an instrument is well-protected away from the nerve, as they are inserted in and out of the outermost dilating tube 12.

Figure 21:
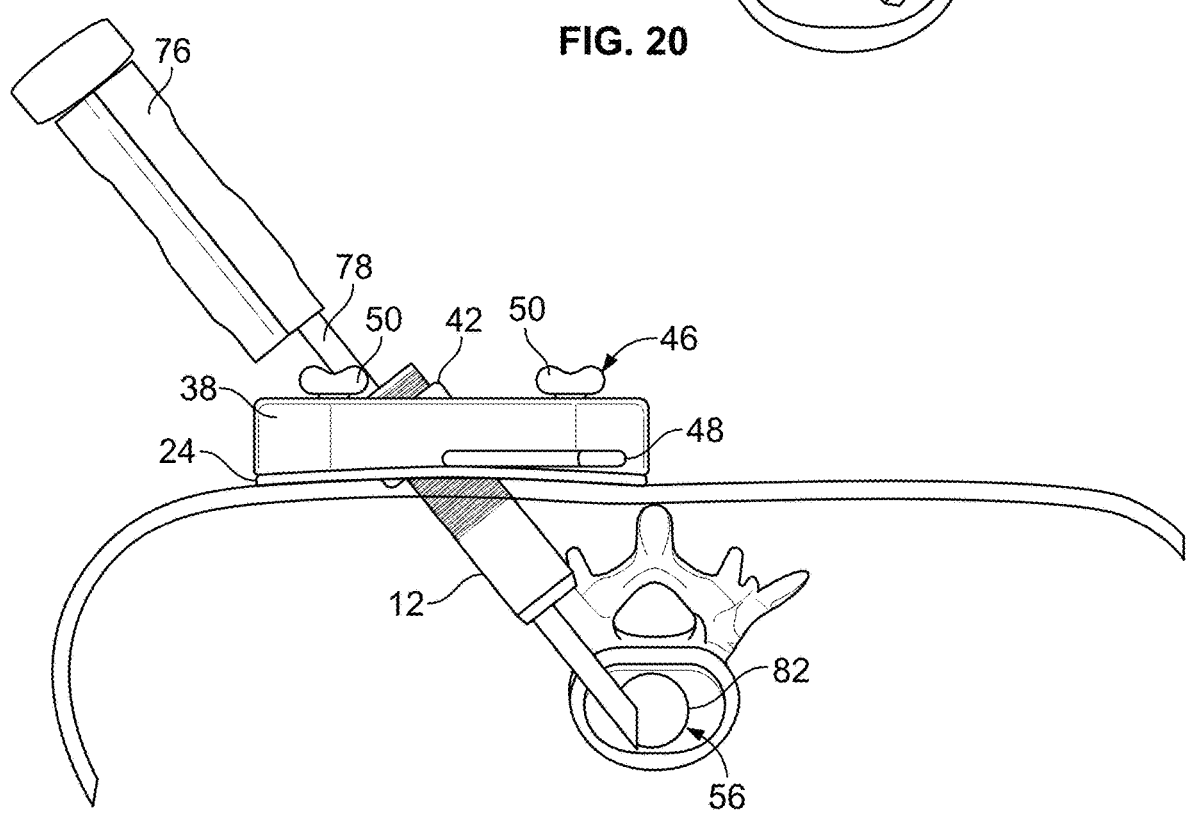
FIG. 21 is an axial view of the system of FIG. 11, showing a discectomy device for removing nucleus material from the disc space and preparing the vertebral endplates for fusion.
Figure 22:
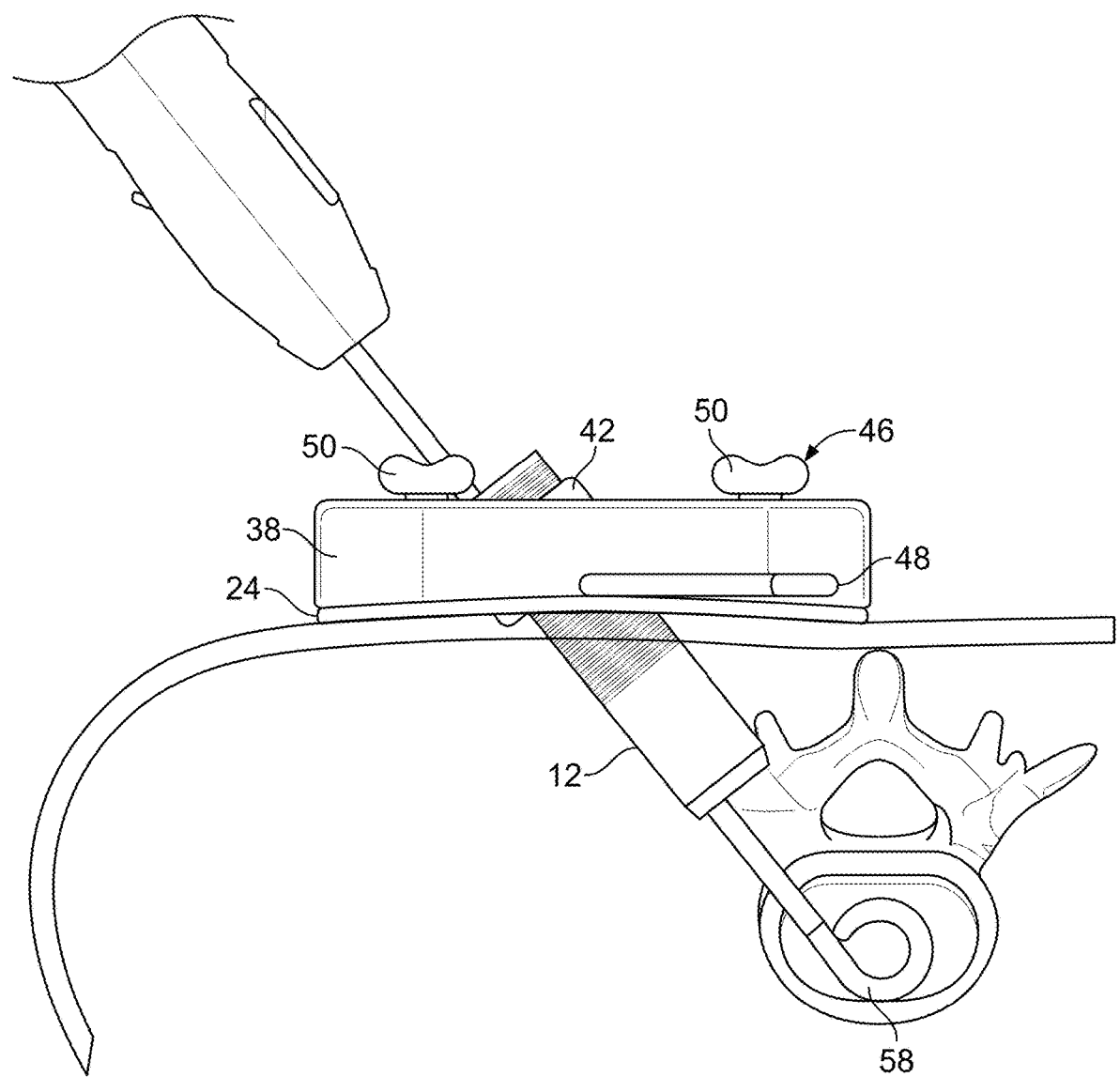
FIG. 22 is an axial view of the system of FIG. 11, showing an implant being deployed into the disc space.

Following the clearing out of the straight access into the disc, additional tools can be used to remove the nucleus material more laterally of the access line either on the ipsilateral side or contra-lateral side, as shown in FIG. 21. In one embodiment, a discectomy device or surgical site preparation device 56 including an elongated barrier defining a working region may be employed. Such a discectomy device 56 may be provided as shown and described in U.S. Patent Application Publication No. 2016/0008141 to Huffmaster et al., which is hereby incorporated herein by reference (and which may device be referred to as the barrier/GuardRail system of Benvenue Medical, Inc. of Santa Clara, Calif.). Upon completion of the nucleus material removal and preparation of the endplate, an implant 58 such as the LUNA® 360 of Benvenue Medical, Inc. can be deployed in the disc space for re-establishing proper height and lordosis, as in FIG. 22.

Figure 23:
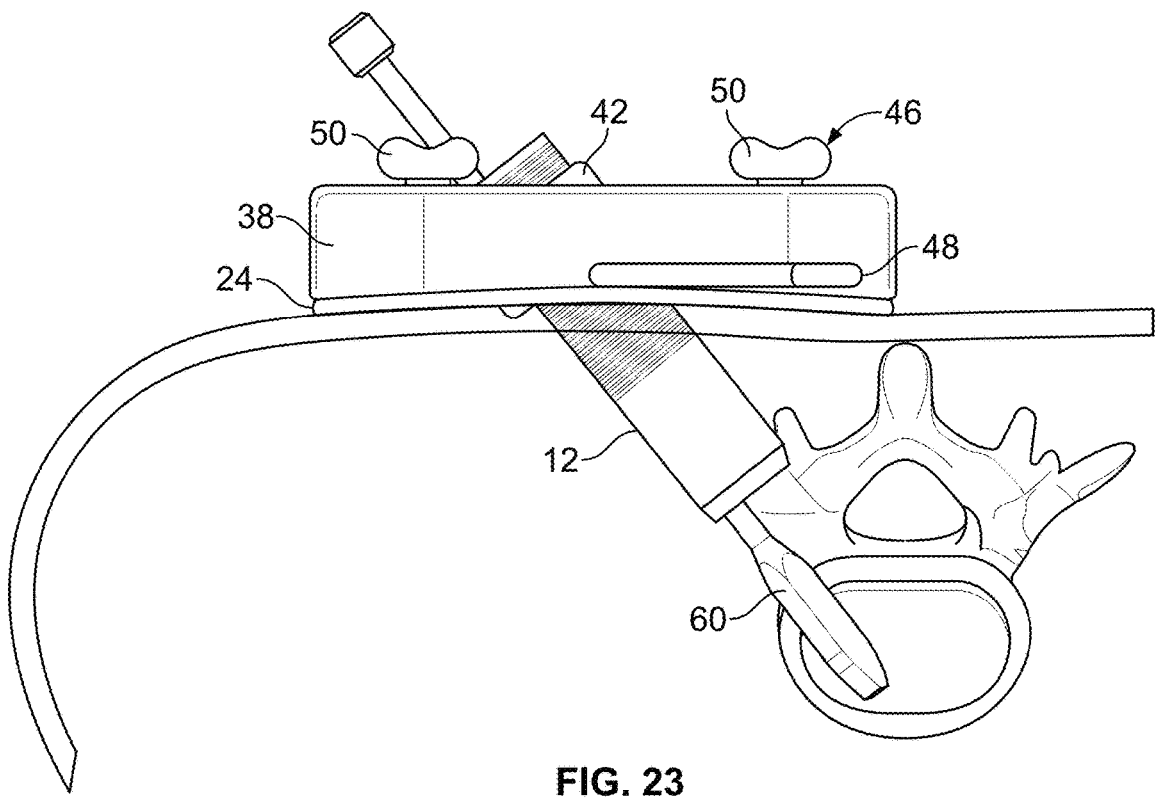
FIG. 23 is an axial view of the system of FIG. 11, showing a wedge distractor engaged into the disc space through the dilating tube.
Figure 24:
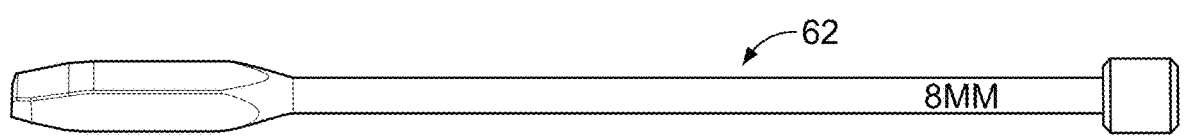
FIGS. 24-26 are side elevational views of exemplary wedge distractors.
Figure 25:
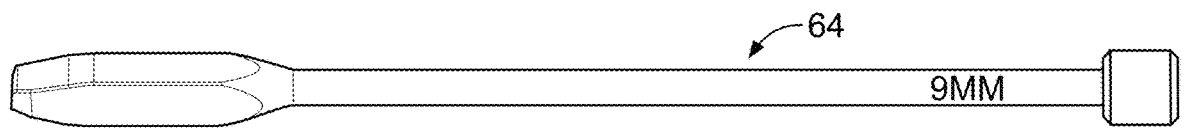
Figure 26:
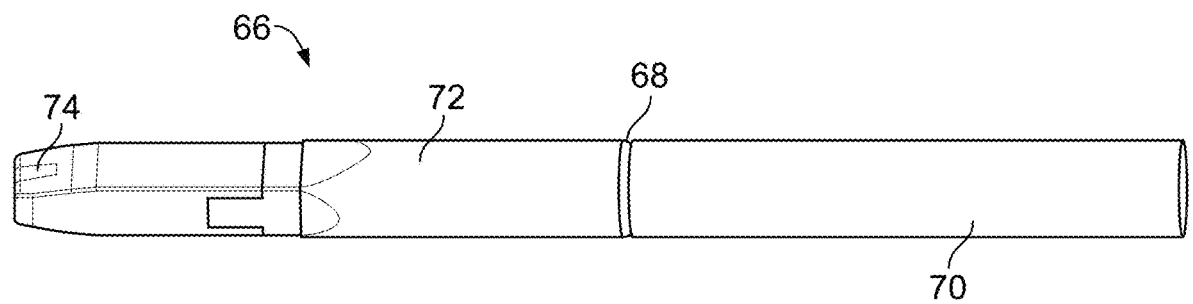

FIG. 23 shows an exemplary wedge distractor 60 that can be inserted into the disc through the outermost dilating tube 12 of the disclosed access system 10 for preparing the disc, prior to insertion of the implant 58. Additional wedge distractors 62-66 (FIGS. 24-26) can be inserted incrementally to distract the disc space to the desired shape. For example, it is fairly standard in practice to start with a wedge distractor of a size of 3 mm for a much collapsed disc and proceed to use wedge distractors with increasing size (up to a 9 or 10 mm, in one embodiment) in order to get the proper re-alignment of that particular spine level.

Figure 27:
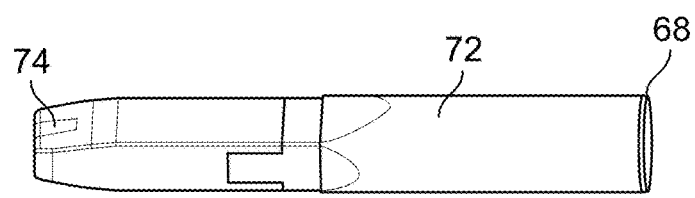
FIG. 27 is a detail view of the tip of the wedge distractor of FIG. 26, once separated.

These wedge distractors can be malleted to the desired position and retrieved using a slap hammer that is common in the field. In one embodiment, the final distractor 66 (FIG. 26) is made slightly differently, as it has a coupling 68 along a shaft 70 that can be disconnected once in place (FIG. 27). The coupling 68 of the final wedge distractor 66 may vary without departing from the scope of the present disclosure, but could be a simple threaded connection in one embodiment.

Figure 28:
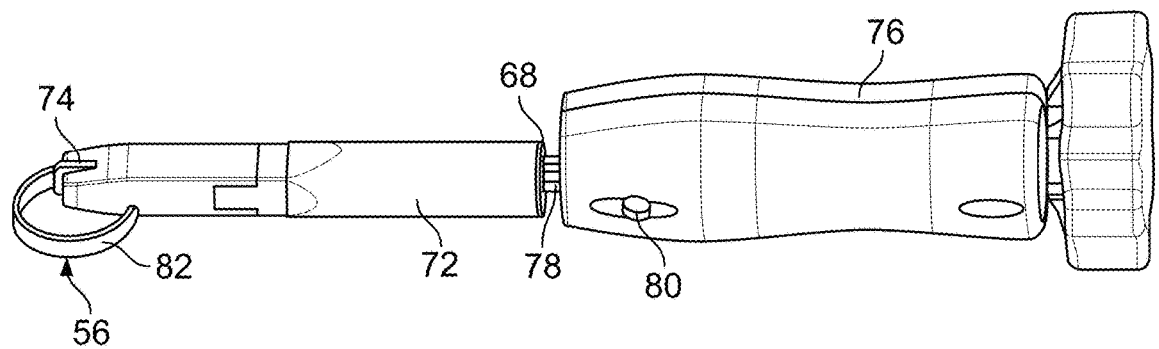
FIG. 28 is a side elevational view of the combination of the tip of the wedge distractor of FIG. 27 and a device for delivering a discectomy device.
Figure 29:
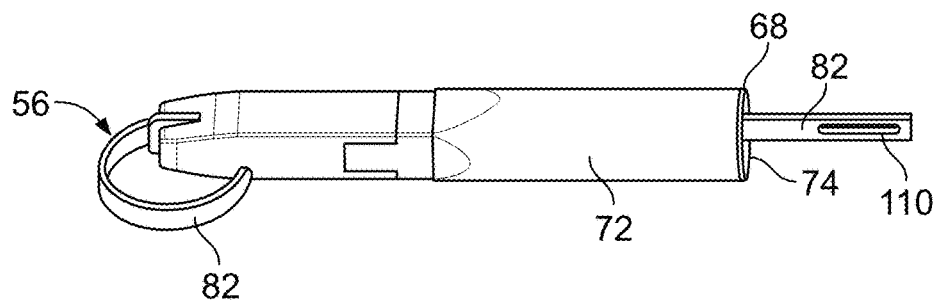
FIG. 29 is a side elevational view of the combination of FIG. 28, with the delivery device being removed, and the discectomy device and the tip of the wedge distractor remaining.

As shown in FIG. 27, once disconnected, the distractor tip 72 has an opening 74 to allow insertion of a site preparation device or discectomy device 56, which may be of the type shown in FIG. 21 (e.g., the barrier/GuardRail system of Benvenue Medical, Inc.). In one embodiment, an assembly 76 for delivering such a discectomy device 56 includes a delivery cannula 78, as can be seen in FIG. 28. The delivery assembly 76 is configured to deploy the discectomy device 56 (which may be configured as a shaped-set ribbon) and includes means 80 to disconnect the delivery assembly 76 from the discectomy device 56, leaving only a distal portion 82 of the discectomy device 56 in place to define a working region within the disc space, as shown in FIG. 29.

Figure 30:
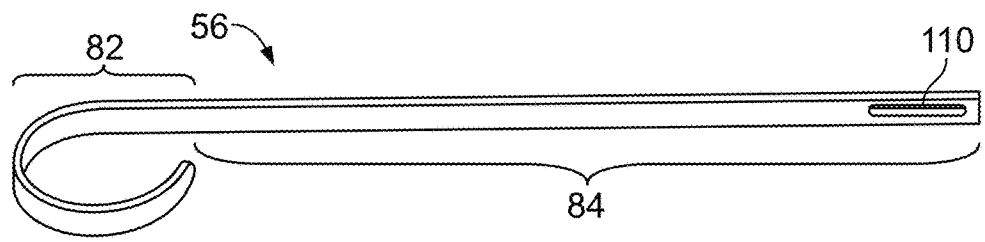
FIG. 30 is a side elevational view of the discectomy device of FIG. 29, with the tip of the wedge distractor omitted.
Figure 31:
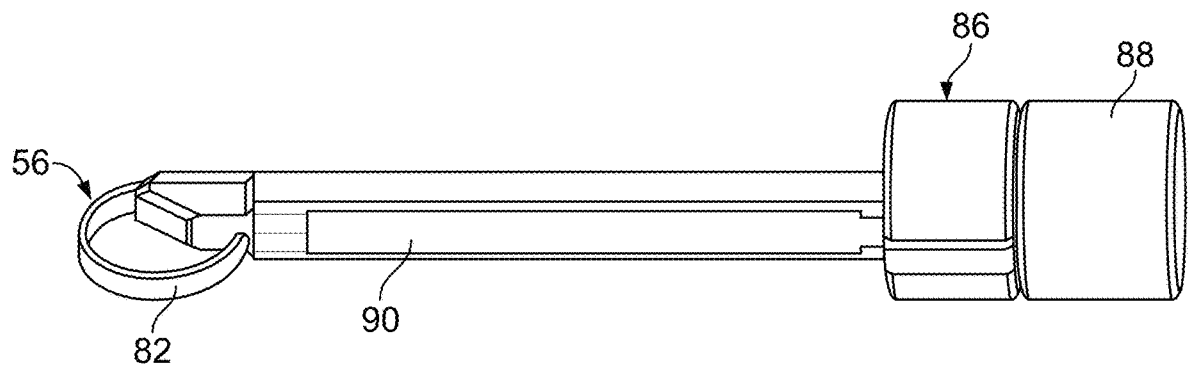
FIG. 31 is a side elevational view of the discectomy device of FIG. 30, with an associated access tube and obturator.
Figure 32:
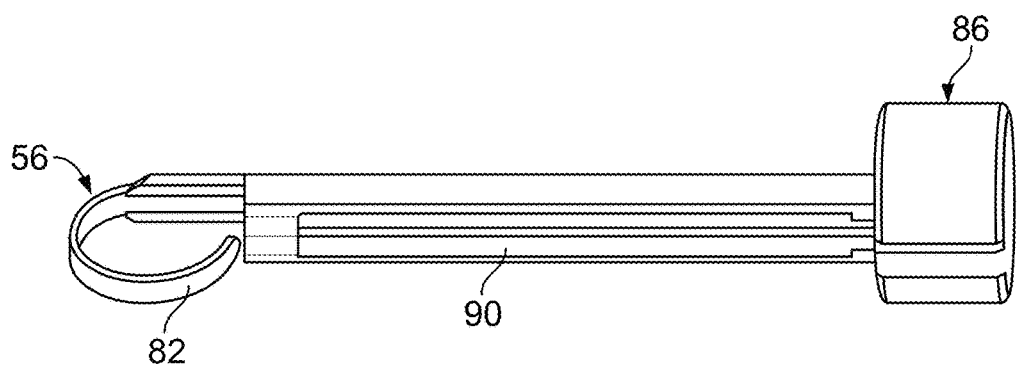
FIG. 32 is a side elevational view of the assembly of FIG. 31, with the obturator omitted.
Figure 33:
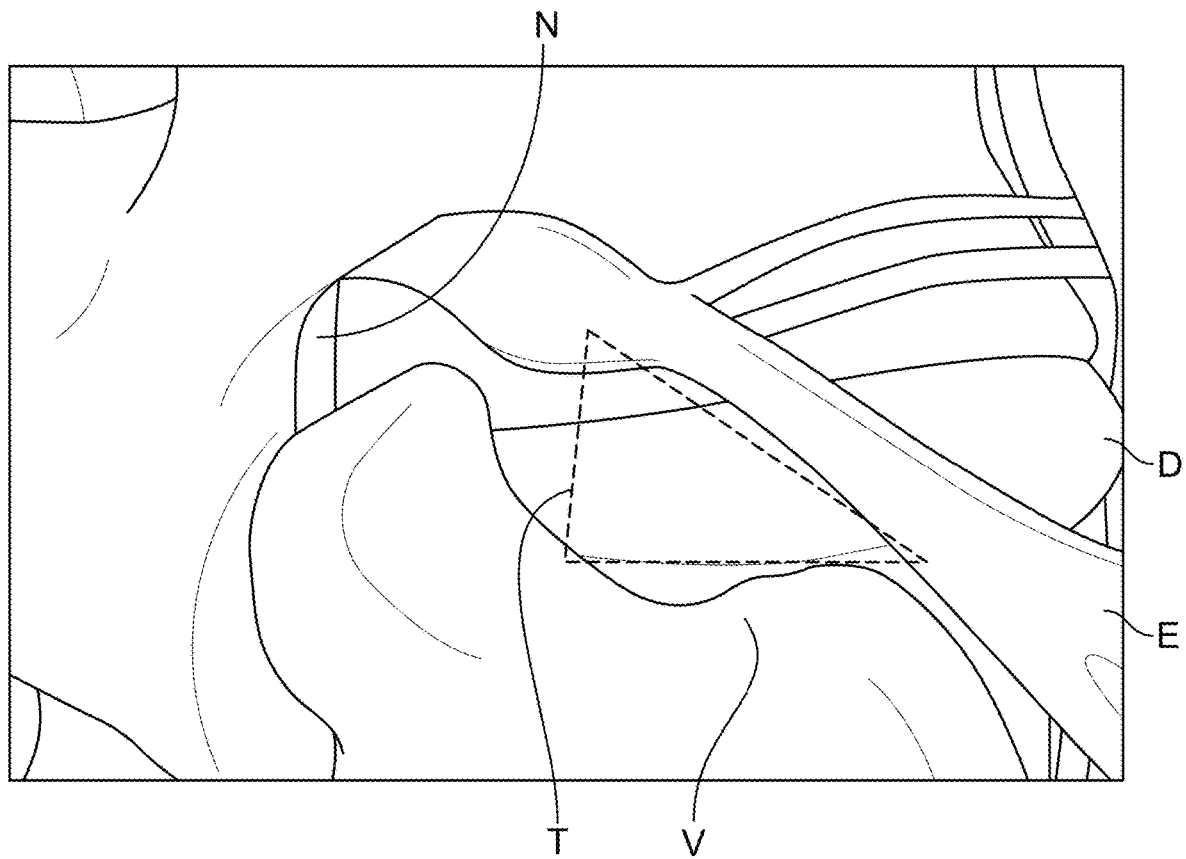
FIG. 33 is a lateral view showing Kambin's triangle.

As can be seen in FIG. 30, the discectomy device 56 may include a distal portion 82 positioned within the surgical site and a guide portion or proximal portion 84 that remains outside of the surgical site. As shown in FIG. 31, an access tube 86 with an obturator 88 can be introduced over the proximal portion 84 of the discectomy device 56 to provide a much larger access pathway for tools to complete the discectomy and nucleus removal once the obturator 88 is removed (FIG. 32). In the illustrated embodiment, a distal end opening of the access tube 86 is aligned with the opening leading into the working region defined by the discectomy device 56 so that discectomy and disc space preparation tools can be inserted through the access tube 86 and into the working region. The distal portion 82 of the discectomy device 56 protects surrounding tissue during the discectomy and disc space preparation, which may include the insertion of multiple tools and/or multiple passings of a tool.

The access tube 86 may include a side cut 90 along the lateral aspect so that one can advance an articulated tool or angled device without being too constrained, as would be the case with a fixed tube.

Figure 38:
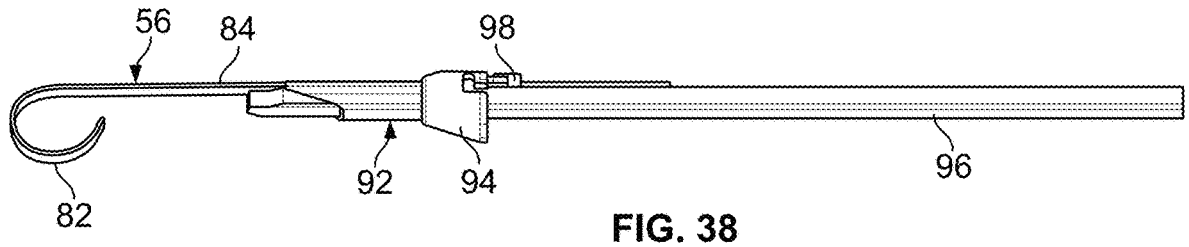
FIG. 38 is a side elevational view of another embodiment of an access tube, with an associated obturator.
Figure 39:
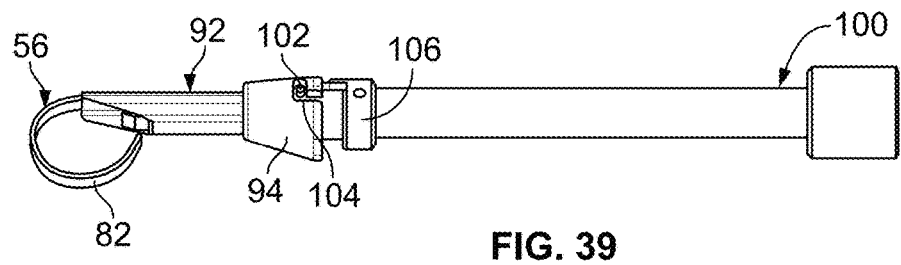
FIGS. 39 and 40 are side elevational views of the access tube of FIG. 38, with an associated driver-remover tool.
Figure 40:
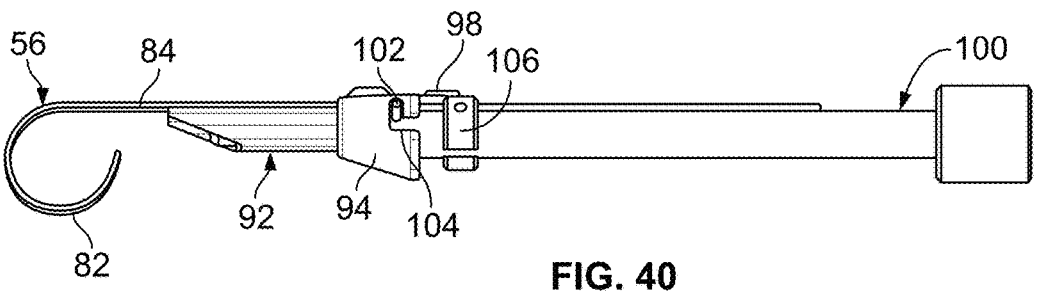

Another configuration of an access tube is shown in FIGS. 38-41. In the embodiment of FIG. 38, the access tube 92 is relatively short compared to the access tube 86 of FIGS. 31 and 32, but has an enlarged funnel 94 to allow for docking of additional instruments. As a first step, an obturator 96 would be used to first position the access tube 92 in place through the soft tissue. The access tube 92 may be keyed to the proximal portion 84 of the associated site preparation or discectomy device 56 by a snap-lock feature 98, with the distal portion 82 of the site preparation device 56 being deployed to the disc space when the access tube 92 has been properly positioned. Alternatively, the distal portion 82 of the site preparation device 56 may be at least partially positioned within the disc space, followed by the access tube 92 being advanced along the proximal portion 84 of the site preparation device 56 (which remains outside of the disc space) and into position. In either case, a driver-remover tool 100 may be connected to the access tube 92, as shown in FIGS. 39 and 40, with engaging pins 102 of the tool 100 being received in corresponding recesses 104 in the enlarged funnel 94 for moving the access tube 92 into working position. A collar feature 106 may be used to key-in to the proximal portion 84 of the site preparation device 56 during the placement to the working position as shown in FIG. 39 and can be rotated in such position that it would disengage the snap-lock feature 98 of the access tube 92 (as in FIG. 40), followed by removal of the tool 100 (e.g., by using a slap hammer technique).

Figure 41:
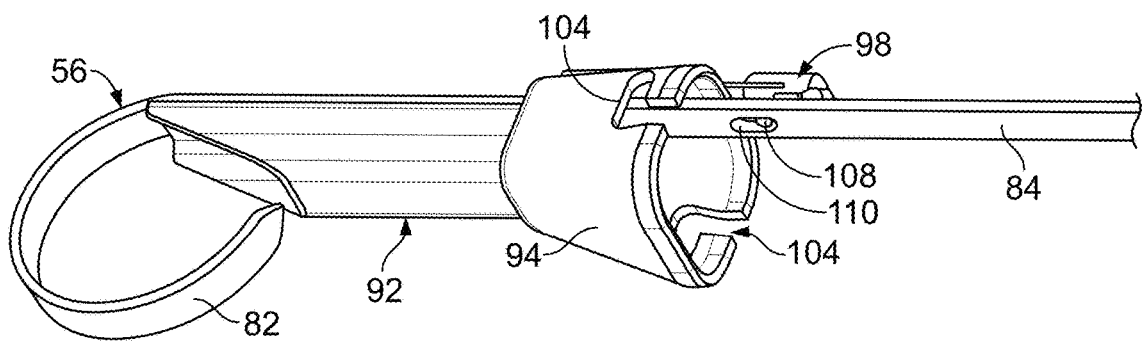
FIG. 41 is a detail view of the access tube of FIG. 38, with an associated site preparation device.

FIG. 41 shows an enlarged image of the access tube 92 with a more detailed view of the corresponding recess or recesses 104 for aiding in the placement or removal of the access tube 92 as previously explained or any other tools that might need to be connected to the access tube 92 during a procedure for preparing the disc, inserting an implant, or placing bone graft material. It can also be seen that the snap-lock feature 98 may have a pin 108 to engage in a corresponding hole 110 of the proximal portion 84 of the site preparation device 56 for locking the device 56 to the access tube 92 in the working position.

Exemplary Method

A minimally invasive posterior, interbody fusion technique is based on creating an access corridor to the intervertebral disc space by removing the superior articular process via the transmuscular, tubular retractor system described above. The use of such a system is described below as it would be conducted in a surgical setting.

Following the induction of general anesthesia, the patient is positioned prone on a radiolucent operating room table, with a focus on positioning to maximize lordosis. Fluoroscopy is utilized throughout the procedure for radiographic guidance. After preparation of the surgical site with the above-mentioned guidance, the access target is identified and the skin based gel pad is put into place after removing the peel-away sheet to expose the adhesive backing so the gel pad can stick to the skin of the patient with the target entry point in the middle of the cut-out. This determines where the skin cut-out access will be made in order to optimize the best trajectory to the disc for this particular approach.

A one inch paramedian incision is created, at the target location which is about 3-4 cm off the midline. A muscle-splitting corridor is created through the paraspinal muscles and an 10-28 mm tubular retractor is inserted and docked (as explained previously), followed by the positioning of the dilating tubes until exposure of the facet joint line in its medial aspect, the superior articular process at the center, and the extraforaminal zone laterally (FIGS. 9, 15, and 18). The facet joint line is defined with electrocautery, and an osteotome or high speed drill is used to create a trough across the base of the superior articular process, just above the inferior pedicle. An osteotome is placed into the facet joint line and rotated to fracture the superior articular process, which is then removed. Additional care is taken to minimize damage to structures such as the intertransverse ligament/ligamentum flavum in order to expose the exiting nerve root and the disc space. The exiting nerve root "E" is gently elevated with suction and the disc space is entered via Kambin's triangle "T" (see FIG. 33), which is defined by the exiting nerve root "E", the traversing nerve root "N", and the vertebral body "V".

Upon access to the disc space, discectomy and endplate preparation is completed with any suitable tools, which may include the discectomy or site preparation device previously described. The discectomy or site preparation device may be provided as a barrier/GuardRail system of the type described in greater detail in U.S. Patent Application Publication No. 2016/0008141 to Huffmaster et al.

In some specific anatomies, the disc height will have to be elevated first, such as by the use of a series of distractors (such as those of the type that are inserted into the disc space and rotated) to restore disc height. One suitable approach for sizing and/or spacing apart the facing vertebral endplates is described in U.S. Patent Application Publication No. 2016/0256148 to Huffmaster et al., which is incorporated herein by reference.

Additionally, in some cases, additional contralateral distraction will be required using percutaneous pedicle screws and rod to maintain the height restoration during discectomy and during the placement of the interbody device.

Upon completion of the discectomy and endplate preparation, the insertion and deployment of the interbody device is performed to restore disc height, leading to ligamentotaxis and indirect decompression of the central spinal canal and contralateral foramen. This may include the insertion of a multidimensional, expanding interbody device, such as the LUNA® 360 of Benvenue Medical, Inc., aspects of which are described in U.S. Pat. No. 8,454,617 to Schaller et al. and U.S. Pat. No. 9,480,574 to Lee et al., which are incorporated herein by reference.

When the implant has been deployed, bone graft material may be inserted into the disc space according to any suitable approach, including the approach described in U.S. Patent Application Publication No. 2016/0228261 to Emery et al., which is incorporated herein by reference.

Upon completion of the interbody placement and introduction of bone graft material, posterior rigid fixation may be achieved by placement of percutaneous pedicle screws.

Finally, the site may be closed.

Second Exemplary System and Method

Figure 34:
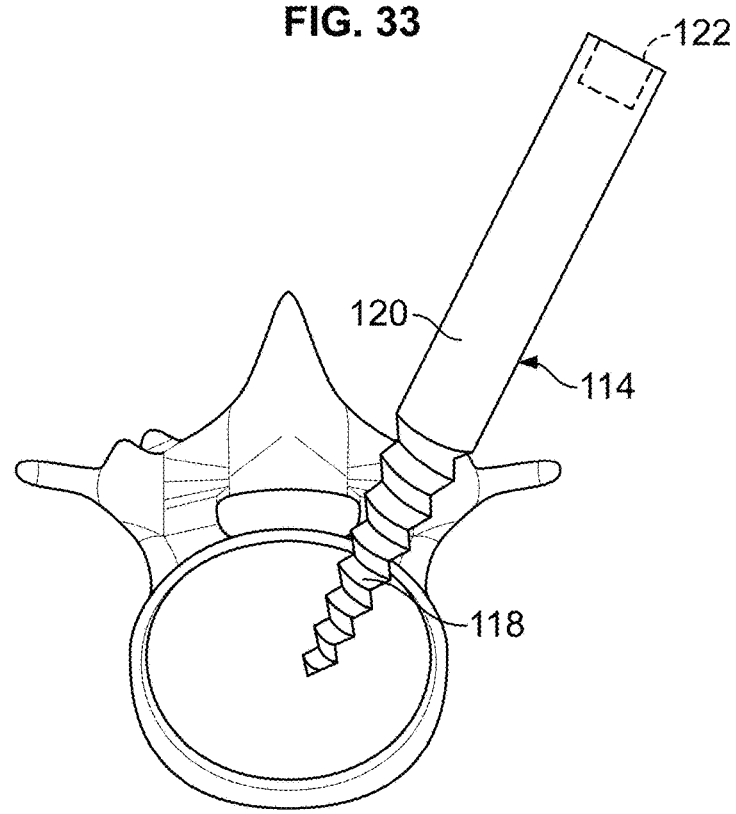
FIG. 34 is an axial view of a modified pedicle tap of a pedicle-based retractor system for accessing a vertebral disc space.
Figure 35:
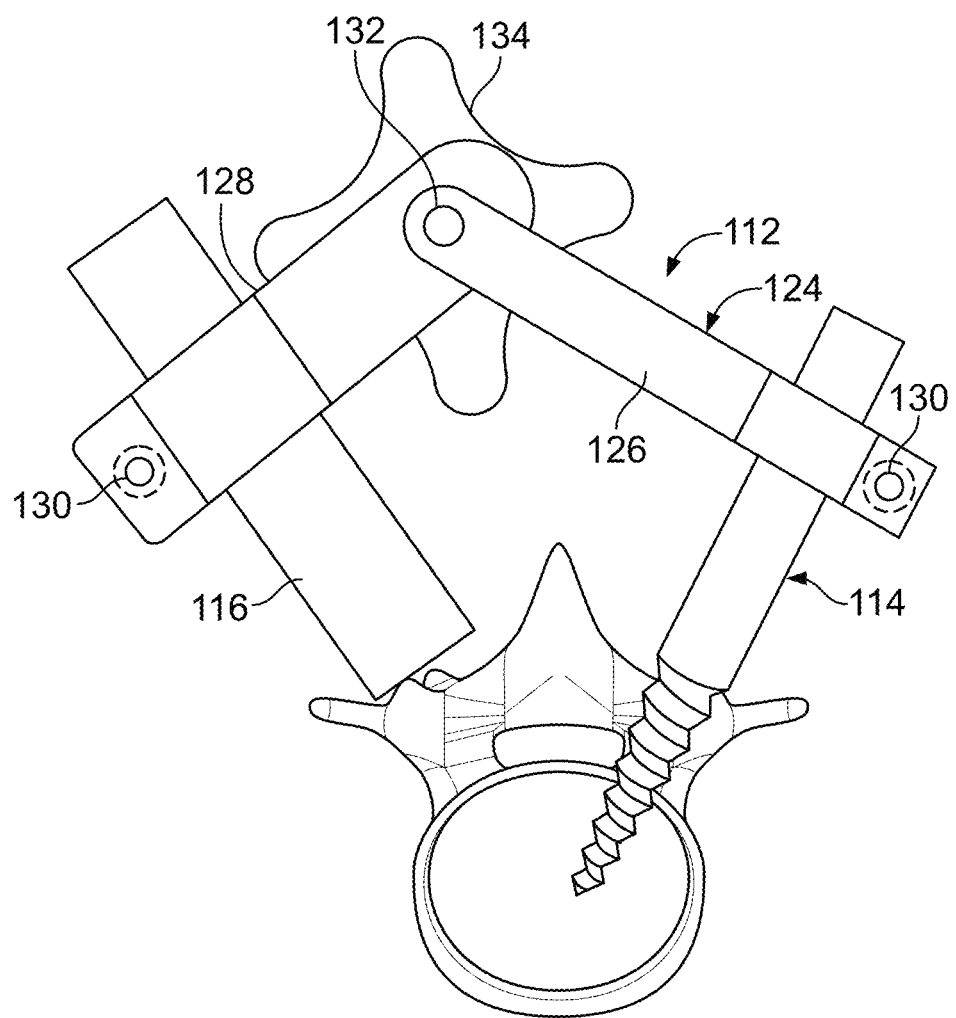
FIG. 35 is an axial view of the modified pedicle tap and vertebral disc space of FIG. 34, showing a holding arm assembly and dilating tube associated with the modified pedicle tap.
Figure 36A:
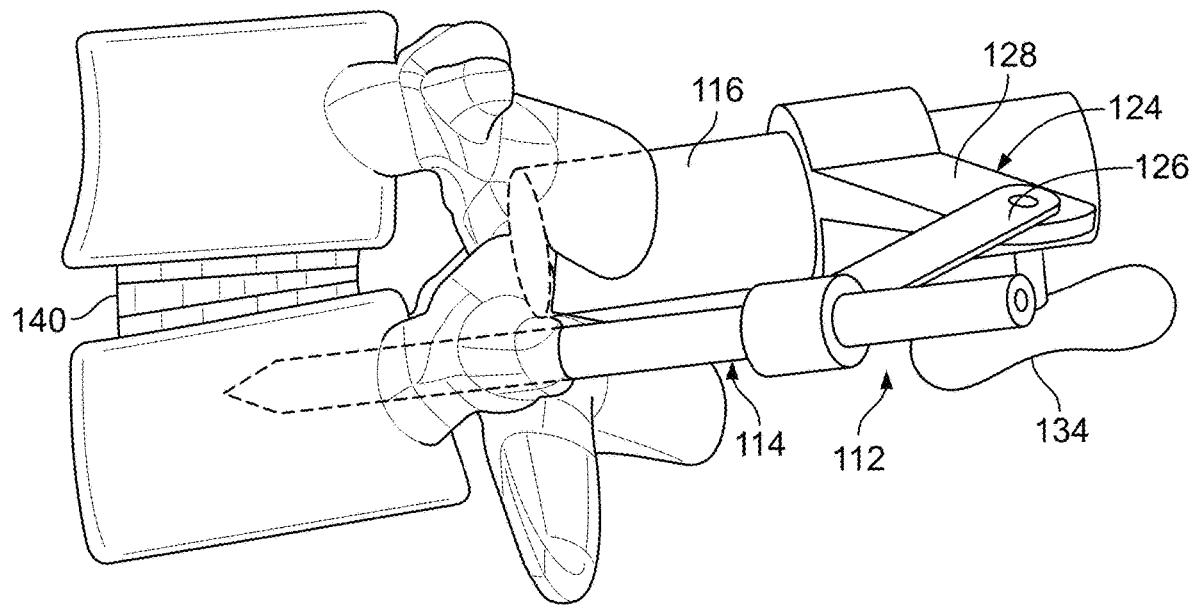
FIG. 36A is a lateral view of the pedicle-based retractor system of FIG. 35, secured to a spine segment.

FIGS. 34-36A show an alternative mounting system 112 and associated method. In this embodiment, a pedicle-based retractor system 112 includes a modified pedicle tap 114 that may be used at the opposite side of the entry site of the surgery access and anchored into a pedicle to hold a dilating tube 116 (which may be configured similarly to the outermost dilating tube 12) in place (FIGS. 35 and 36A). The modified pedicle tap 114 comprises a small size pedicle screw thread at a distal portion 118 and an extended, removable posterior section shaft 120, including a recess 122 for a set screw handle at its proximal end (FIG. 34).

As shown in FIG. 34, the modified pedicle tap 114 is first secured to a pedicle. With the modified pedicle tap 114 so secured to the pedicle, the rest of the system 112 may be assembled and positioned with respect to the disc space. In particular, FIG. 35 shows the modified pedicle tap 114 connected to the dilating tube 116 by a holding arm assembly 124. In the illustrated embodiment, the holding arm assembly 124 comprises a first holding arm 126 removably connected to the modified pedicle tap 114 and a second holding arm 128 removably connected to the dilating tube 116. Each holding arm 126, 128 may include a clamp mechanism 130 for removably securing the first holding arm 126 to the modified pedicle tap 114 and the second holding arm 128 to the dilating tube 116. The holding arms 126 and 128 of the illustrated embodiment are connected together at a joint 132 including a swivel knob 134, which allows the holding arms 126 and 128 to be pivoted with respect to each other into a desired orientation. When the holding arms 126 and 128 have been moved into the desired orientation, the swivel knob 134 may be actuated (e.g., by being rotated) to lock the holding arms 126 and 128 in place. It may be advantageous for the holding arms 126 and 128 to be relatively short, which may allow for improved holding power and rigidity compared to longer holding arms. In other embodiments, rather than comprising a pair of holding arms, the holding arm assembly may comprise a single holding arm or more than two holding arms.

Figure 36B:
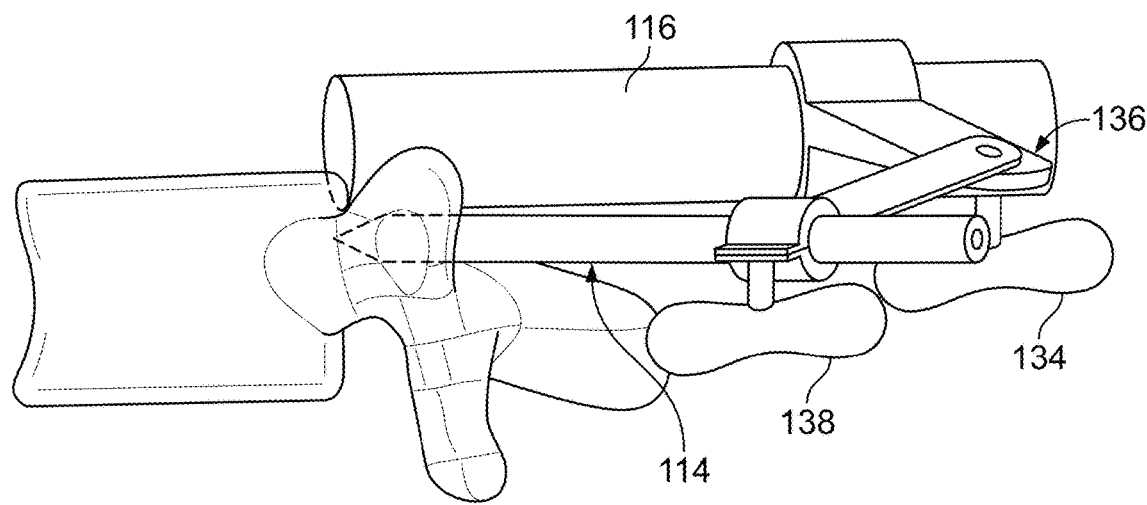
FIG. 36B is a lateral view of the modified pedicle tap and dilating tube of FIG. 35, joined by an alternative embodiment of a holding arm assembly.

FIG. 36B illustrates an alternative embodiment in which the modified pedicle tap 114 and dilating tube 116 are connected by a differently configured holding arm assembly 136. In the embodiment of FIG. 36B, each of the clamp mechanisms is provided with an associated swivel knob 138, which allows for additional adjustment of the orientation of the modified pedicle tap 114 and dilating tube 116 with respect to the disc space.

Once the dilating tube 116 has been mounted in place, with any smaller-diameter dilating tubes removed, the procedure may be carried out in general accordance with the foregoing description of the method of using the first exemplary system.

Figure 37:
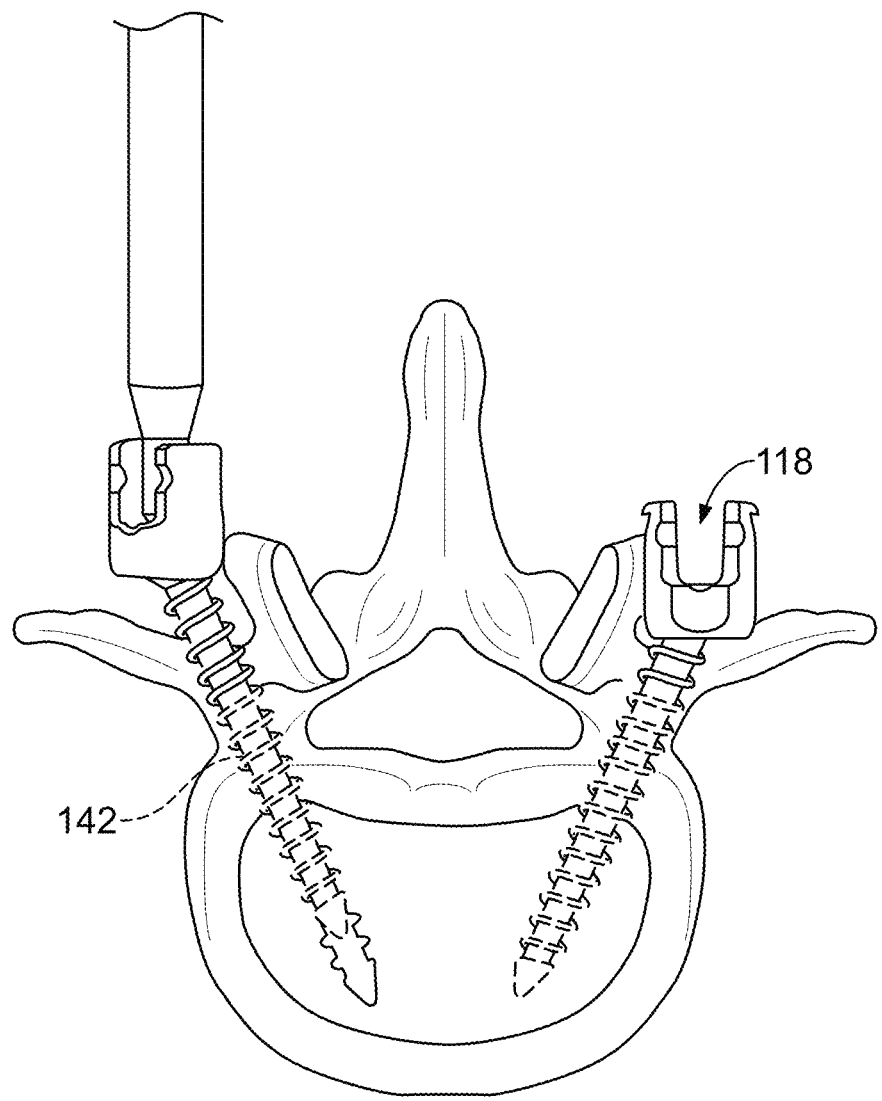
FIG. 37 is an axial view of a final posterior fixation screw set.

FIG. 36A shows the system 112 of FIG. 35, with an implant 140 fully inserted into the disc space, prior to removal of the modified pedicle tap 114, dilating tube 116, and holding arm assembly 124. Subsequently, the dilating tube 116 and holding arm assembly 124, along with the proximal portion or shaft 120 of the modified pedicle tap 114, may be removed, leaving the distal portion 118 of the modified pedicle tap 114. The dilating tube 116 may be replaced with a standard pedicle screw 142, along with standard screws and the like to provide mobilization of the particular spinal segment (FIG. 37). In an alternative embodiment, the entire modified pedicle tap 114 may be removed and replaced with a standard pedicle screw 142, which may have a larger threaded distal section than the modified pedicle tap 114.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A minimal impact access system for accessing a vertebral disc space comprising:
   a pad configured to be secured to a skin surface of a patient and defining an opening;
   a retractor frame secured with respect to the pad and defining an opening at least partially aligned with the opening of the pad;
   a swivel base configured to be secured with respect to the pad and including a swivel at least partially aligned with the openings of the pad and the retractor frame; and
   an outermost dilating tube received by the swivel for pivotal movement with respect to the pad and defining a corridor for accessing the vertebral disc space of the patient, wherein
   a position of the swivel base with respect to the pad and to the retractor frame is adjustable prior to the swivel base being secured with respect to the pad, and
   the retractor frame includes a lever configured to be actuated to produce a sucking action between the pad and the swivel base to releasably secure the swivel base with respect to the pad.

2. The minimal impact access system of claim 1, further comprising an elongated guide configured to facilitate positioning of the outermost dilating tube with respect to the pad.

3. The minimal impact access system of claim 2, further comprising a plurality of inner dilating tubes, wherein
   each inner dilating tube has a different diameter,
   the diameters of the inner dilating tubes are smaller than a diameter of the outermost dilating tube, and
   the inner dilating tubes are configured to be sequentially advanced over the elongated guide prior to advancement of the outermost dilating tube over the elongated guide and the inner dilating tubes.

4. The minimal impact access system of claim 1, wherein the outermost dilating tube comprises a distal end including at least one impaction tooth or anchoring spike.

5. The minimal impact access system of claim 1, wherein the elongated guide comprises an osteotome.

6. The minimal impact access system of claim 1, wherein the elongated guide comprises a metallic pin including a threaded distal tip.

7. The minimal impact access system of claim 1, wherein the pad comprises a gel pad including an adhesive backing.

8. A minimal impact access system for accessing a vertebral disc space comprising:
   a pad configured to be secured to a skin surface of a patient and defining an opening;
   a retractor frame secured with respect to the pad and defining an opening at least partially aligned with the opening of the pad;
   a swivel base including a swivel at least partially aligned with the openings of the pad and the retractor frame;
   a clamping ring plate secured over the swivel base to secure the swivel base with respect to the pad; and
   an outermost dilating tube received by the swivel for pivotal movement with respect to the pad and defining a corridor for accessing the vertebral disc space of the patient, wherein a position of the swivel base with respect to the pad and to the retractor frame is adjustable prior to the swivel base being secured with respect to the pad.

9. A method for accessing a vertebral disc space comprising:
   applying a pad to a skin surface of a patient, the pad defining an opening;
   creating an access in the skin surface within the opening;
   advancing an elongated guide through the access to a target location;
   advancing an outermost dilating tube over the elongated guide;
   advancing a retractor frame and a swivel base over the outermost dilating tube, the retractor frame defining an opening at least partially aligned with the opening of the pad and the swivel base including a swivel at least partially aligned with the openings of the pad and the retractor frame;
   securing the retractor frame and the swivel base with respect to the pad; and
   creating an access into the vertebral disc space through the outermost dilating tube, wherein a position of the swivel base with respect to the pad and to the retractor frame is adjusted prior to securing the swivel base with respect to the pad.

10. The method of claim 9, wherein the target location comprises a facet joint.

11. The method of claim 9, wherein the target location comprises a superficial aspect of a joint line.

12. The method of claim 9, wherein the target location comprises a vertebral disc.

13. The method of claim 9, wherein the guide is advanced to the target location via Kambin's triangle.

14. The method of claim 9, further comprising
   advancing a plurality of inner dilating tubes of successively increasing diameter over the elongated guide, wherein said advancing the outermost dilating tube over the elongated guide includes advancing the outermost dilating tube over the inner dilating tubes, and
   removing said plurality of inner dilating tubes prior to said creating the access into the vertebral disc space through the outermost dilating tube.

15. The method of claim 9, further comprising adjusting an angle of the outermost dilating tube with respect to the pad after said securing the retractor frame and the swivel base with respect to the pad.

16. The method of claim 9, wherein said advancing the outermost dilating tube over the elongated guide includes advancing at least one impaction tooth or anchoring spike at a distal end of the outermost dilating tube into the target location.

17. The method of claim 9, further comprising advancing a clamping ring plate over the elongated guide and over the swivel base to secure the swivel base with respect to the pad.

18. The method of claim 9, further comprising actuating a lever of the retractor frame to produce a sucking action between the pad and the swivel base to releasably secure the swivel base with respect to the pad.

19. The method of claim 9, further comprising adjusting a position of the outermost dilating tube with respect to the pad in a plane defined by the pad.

* * * * *